(12) United States Patent
Dickinson et al.

(10) Patent No.: US 6,583,162 B1
(45) Date of Patent: *Jun. 24, 2003

(54) 2-PYRIDINYLGUANIDINE UROKINASE INHIBITORS

(75) Inventors: Roger Peter Dickinson; Christopher Gordon Barber, both of Sandwich (GB)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/546,410

(22) Filed: Apr. 10, 2000

(30) Foreign Application Priority Data

Apr. 13, 1999 (GB) .............................................. 9908410

(51) Int. Cl.$^7$ ...................... A61K 31/44; C07D 213/00; C07D 213/60; C07D 213/61; C07D 213/72
(52) U.S. Cl. ...................... 514/352; 514/344; 514/357; 546/286; 546/304; 546/306; 546/341; 546/345
(58) Field of Search ................................. 514/344, 352, 514/357; 546/286, 304, 306, 341, 345

(56) References Cited

U.S. PATENT DOCUMENTS

| | | | | |
|---|---|---|---|---|
| 2,604,473 A | 7/1952 | Sperber et al. | ............. | 260/250 |
| 2,713,048 A | 7/1955 | Weston | ..................... | 260/294.8 |
| 4,465,851 A | 8/1984 | Muramatsu et al. | ........ | 560/125 |

FOREIGN PATENT DOCUMENTS

| | | | |
|---|---|---|---|
| DE | 2557438 | * | 6/1976 |
| DE | 25 57 438 | | 6/1976 |
| DE | 19544686 | * | 6/1997 |
| EP | 1 044 967 A3 | | 3/2000 |
| WO | WO 94/26715 | | 11/1994 |
| WO | WO 95/06034 | | 3/1995 |
| WO | 9506034 | * | 6/1997 |
| WO | WO 98/06398 | | 2/1998 |

OTHER PUBLICATIONS

P.J.Taylor et al "Delta–1 values for heterocyles";J.Che.Soc.Perkin Trans.11,1765–70(1986).*
M.Dukat et al" Structure–Activity rel. for the Binding of arylpiperazines . . .";J.Med.Chem.39,4017–26(1996).*
Bioorganic & Medicinal Chemistry Letters 10 (2000) 983–987—Synthesis and Biological Activity of Peptidyl Aldehyde Urokinase Inhibitors.
Heechung, Yang, et al, J. Med. Chem., 1990, vol. 33, pp. 2956–2961.
Scialdone, Mark A., et al, "Phosgenated p–Nitrophenyl(polystyrene)ketoxime or Phoxime Resin. A New Resin for the Solid–Phase Synthesis of Ureas via Thermolytic Cleavage of Oxime–Carbamates", J. Org. Chem., 1998, vol. 63, pp. 4802–4807.
Trapani, Giuseppe, et al, "Novel 2–Phenylimidazo[1,2–a] pyridine Derivatives as Potent and Selective Ligands for Peripheral Benzodiazepine Receptors: Synthesis, Binding Affinity, and in Vivo Studies", J. Med. Chem., 1999, vol. 42, pp. 3934–3941.
Constable, E.C., Jacs, vol. 119, 1997, pp. 5606–5617 –Reed from STIC.
Chang–Sik, Kim, et al, "Rapid Bergman Cyclization of 1,2–Diethynylheteroarenes", J. Org. Chem., 1998, vol. 63, pp. 8229–8234.
Dukat, Malgorzata, et al, "Structure–Activity Relationships for the Binding of Arylpiperazines and Arylbiguanides at 5–Ht3 Serotonin Receptors", J. Med. Chem., 1996, vol. 39, pp. 4017–4026.
Taylor, Peter J., et al, "Values for Herocycles", J. Chem. Soc., Perkin Trans. II, 1986, pp. 1765–1769.
J. Org. Chem., vol. 27, Jul., 1962, pp. 2504–2509 –Reed from STIC.
Chem Abs., 1963, vol. 59, 7498 and 1964, vol. 60, 2983 –Reed from STIC.

* cited by examiner

*Primary Examiner*—Mukund J. Shah
*Assistant Examiner*—Sudhaker B. Patel

(57) ABSTRACT

Compounds of formula (I):

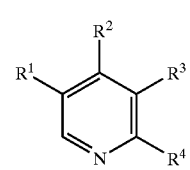

or a pharmaceutically acceptable salt thereof, or solvate of either entity, wherein $R^4$ is a guanidinyl moiety and the other substituents are as defined in the text, are urokinase inhibitors.

12 Claims, No Drawings

2-PYRIDINYLGUANIDINE UROKINASE INHIBITORS

This application claims priority from Great Britain Application GB 9908410.5, filed Apr. 13, 1999.

This invention relates to certain pyridine derivatives useful as urokinase inhibitors, and in particular to 2-diaminomethyleneaminopyridine derivatives, alternatively named as 2-pyridylguanidine derivatives, useful as urokinase inhibitors.

Urokinase (urinary-type plasminogen activator or uPA; International Union of Biochemistry classification number EC.3.4.21.31) is a serine protease produced by a large variety of cell types (smooth muscle cells, fibroblasts, endothelial cells, macrophages and tumour cells). It has been implicated as playing a key role in cellular invasion and tissue remodelling. A principal substrate for uPA is plasminogen which is converted by cell surface-bound uPA to yield the serine protease plasmin. Locally produced high plasmin concentrations mediate cell invasion by breaking down the extracellular matrix. Important processes involving cellular invasion and tissue remodelling include wound repair, bone remodelling, angiogenesis, tumour invasiveness and spread of metastases.

Beneficial effects of urokinase inhibitors have been reported using anti-urokinase monoclonal antibodies and certain other known urokinase inhibitors. For instance, anti-urokinase monoclonal antibodies have been reported to block tumour cell invasiveness in vitro (W. Hollas, et al, *Cancer Res.* 51:3690; A.Meissauer, et al, *Exp. Cell Res.* 192:453 (1991); tumour metastases and invasion in vivo (L. Ossowski, *J. Cell Biol.* 107:2437 (1988)); L. Ossowski, et al, *Cancer Res.* 51:274 (1991)) and angiogenesis in vivo (J. A. Jerdan et al, *J. Cell Biol.* 115[3 Pt 2]:402a (1991). Also, Amiloride™, a known urokinase inhibitor of only moderate potency, has been reported to inhibit tumour metastasis in vivo (J. A. Kellen et al, *Anticancer Res.*, 8:1373 (1988)) and angiogenesis/capillary network formation in vitro (M. A. Alliegro et al, *J. Cell Biol.* 115[3 Pt 2]:402a). Urokinase activity has also been implicated as a factor in psoriasis : Jensen & Lavker (1996) *Cell Growth Diff* 7, 1793–1804 Baker B S and Fry L (1992). *Br J Dermatol,* 126(1), 1–9.2; Spiers E M, et al (1994). *J Invest Dermatol,* 102(3), 333–338.3. Grondahl-Hansen J, et al (1987). *J Invest Dermatol.* 88(1), 28–32. Gissler H, et al (1993). *Br J Dermatol,* 128(6), 612–8; Venning Va., et al (1993). *Clin Exp Dematol,* 18(2), 119–23.

Conditions of particular interest for treatment by urokinase inhibitors include chronic dermal ulcers (including venous ulcers, diabetic ulcers and pressure sores), which are a major cause of morbidity in the ageing population and cause a significant economic burden on healthcare systems. Chronic dermal ulcers are characterised by excessive uncontrolled proteolytic degradation resulting in ulcer extension, loss of functional matrix molecules (e.g. fibronectin) and retardation of epithelisation and ulcer healing. A number of groups have investigated the enzymes responsible for the excessive degradation in the wound environment, and the role of plasminogen activators has been highlighted (M. C. Stacey et al., *Br. J Surgery,* 80, 596; M. Palolahti et al., *Exp. Dermatol.,* 2, 29, 1993; A. A. Rogers et al., *Wound Repair and Regen.,* 3, 273, 1995). Normal human skin demonstrates low levels of plasminogen activators which are localised to blood vessels and identified as tissue type plasminogen activator (tPA). In marked contrast, chronic ulcers demonstrate high levels of urokinase type plasminogen activator (uPA) localised diffusely throughout the ulcer periphery and the lesion, and readily detectable in wound fluids.

uPA could affect wound healing in several ways. Plasmin, produced by activation of plasminogen, can produce breakdown of extracellular matrix by both indirect (via activation of matrix metalloproteases) and direct means. Plasmin has been shown to degrade several extracellular matrix components, including gelatin, fibronectin, proteoglycan core proteins as well as its major substrate, fibrin. Whilst activation of matrix metalloproteases (MMPs) can be performed by a number of inflammatory cell proteases (e.g. elastase and cathepsin G), the uPA/plasmin cascade has been implicated in the activation of MMPs in situ, providing a broad capacity for degrading all components of the extracellular matrix. Furthermore, in addition to its effect on production of plasmin, uPA has been shown to catalyse direct cleavage of fibronectin yielding antiproliferative peptides. Thus, over-expression of uPA in the wound environment has the potential to promote uncontrolled matrix degradation and inhibition of tissue repair. Inhibitors of the enzyme thus have the potential to promote healing of chronic wounds.

Several related enzymes such as tPA, which also acts via production of plasmin, play a key role in the fibrinolytic cascade. Because of this it is desirable that a uPA inhibitor has adequate potency and selectivity for uPA relative to both tPA and plasmin to avoid the possibility of anti-fibrinolytic side effects.

The utility of such potent and selective urokinase inhibitors is highlighted by the broad range of invasive biological processes mediated by urokinase. These processes include, but are not limited to, wound healing, angiogenesis-dependent conditions such as retinopathy, bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis.

Various aromatic amidines have been reported to inhibit uPA (J. D. Geratz, M. C.-F. Cheng, Thromb. Diathes. haemorrh. (Stuttg.), ;3 230, 1975; J. Stürzebecher, F. Markwardt, Pharmazie, 33, 599, 1978; J. D. Geratz et al., Thromb. Res., 24, 73, 1981). The compounds reported in these publications are generally relatively weak and/or non-selective for uPA relative to other related serine proteases. EP 0 568 289 A2 discloses a series of benzo[b]thiophene-2-carboxamidines with significantly greater potency and selectivity with respect to tPA and plasmin (see also M. J. Towle et al., *Cancer Res.,* 53, 2553, 1993; A. J. Bridges et al., *Bioorg. Med. Chem.,* 1, 403, 1993).

There are few reports of guanidine derivatives as uPA inhibitors. Amiloride™ (see below) is a weak but selective inhibitor of uPA (J.-D. Vassalli, D. Belin, *FEBS Letters,* 214, 187, 1987), and various 2-, 3- and 4-substituted phenylguanidines are reported to have a similar level of potency (H. Yang et al., *J. Med. Chem.,* 33, 2956, 1990).

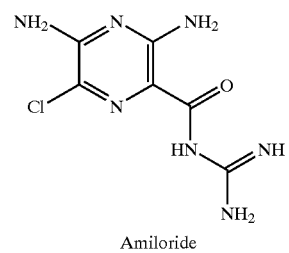

Amiloride

M. Dukat et al, in *J. Med Chem.* 39, 4017 (1996) disclose various arylguanidines as a novel class of 5-HT$_3$ ligands, the disclosure including the compound 2-guanidinopyridine. This compound is also disclosed by P J Taylor et al, in *J. Chem.Soc.Perkin Trans. (II)* 1765 (1986).

The substances described herein are potent reversibly-competitive inhibitors of urokinase enzymatic activity, with selectivity for urokinase relative to certain other important proteases, including the fibrinolytic enzymes tissue-type plasminogen activator (tPA) and plasmin.

The selectivity of the instantly-claimed substances for inhibition of urokinase over inhibition of other proteases such as tPA and plasmin, and the fact that they inhibit reversibly, prevents them from having thrombogenic properties. Thus, according to the present invention, there is provided a compound of formula (I):

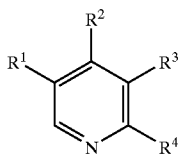

or a pharmaceutically acceptable salt thereof, or solvate of either entity,
wherein
  $R^1$ is H, halogen, CN, $C_{1-6}$ alkyl optionally substituted by one or more halogen, or $C_{1-6}$ alkoxy optionally substituted by one or more halogen,
  $R^2$ and $R^3$ are each independently H, halogen, $C_{1-6}$ alkyl optionally substituted by one or more halogen or $C_{1-6}$ alkoxy, aryl, $(C_n\text{-alkylene})CO_2H$, $(C_n\text{-alkylene})CO_2(C_{1-6}$ alkyl), $(C_n\text{-alkylene})CONR^5R^6$, $CH=CHR^7$, $CH=CHCO_2H$, $CH=CHCONR^5R^6$, $CH=CHSO_2NR^5R^6$, $C=CR^7$, $O(C_m\text{-alkylene})OH$, $O(C_m\text{-alkylene})OR^8$, $OR^8$, $O(C_m\text{-alkylene})CONR^5R^6$, $CH_2OR^8$ or $CH_2NR^5R^6$,
  $R^4$ is $N=C(NH_2)_2$ or $NHC(=NH)NH_2$,
  $R^5$ and $R^6$ are each independently H, $C_{1-6}$ alkyl optionally substituted by OH or $CO_2H$, het($C_{1-6}$ alkylene) or aryl($C_{1-6}$ alkylene), or can be taken together with the nitrogen to which they are attached, to form a 4- to 7-membered saturated ring optionally containing an additional hetero-moiety selected from O, S or $NR^9$, and which ring is optionally benzo-fused,
  and which optionally benzo-fused ring is optionally substituted by up to three substituents independently selected from OH, halogen, $CO_2H$, $CO_2(C_{1-6}$ alkyl) and $C_{1-6}$ alkyl,
  $R^7$ is $C_{1-6}$ alkyl, aryl or het;
  $R^8$ is $C_{1-6}$ alkyl, aryl, het, aryl($CHCO_2H$) or aryl($C_{1-6}$ alkylene);
  $R^9$ is H, $C_{1-6}$ alkyl, or $CO(C_{1-6}$ alkyl);
  wherein "aryl" including the aryl moiety of the aryl($C_{1-6}$ alkylene) group, means phenyl optionally substituted by up to three substituents independently selected from halogen, $C_{1-6}$ alkyl, $(C_n\text{-alkylene})CO_2H$, $(C_n\text{-alkylene})CO_2(C_{1-6}$ alkyl), $(C_n\text{-alkylene})CN$, $C_{1-6}$ alkoxy, CN, $(C_n\text{-alkylene})CONR^5R^6$, $CH=CHCO_2H$, $CH=CHCONR^5R^6$, $CH=CHSO_2NR^5R^6$, $O(C_m\text{-alkylene})OH$, $CH_2NR^5R^6$, and $O(C_m\text{-alkylene})CONR^5R^6$;
  "het" means an optionally benzo-fused 5- or 6-membered saturated or unsaturated heterocycle linked by any available atom in the heterocyclic or benzo-ring (if present), which heterocyclic group is selected from dioxolyl, furyl, thienyl, pyrrolyl, oxazolyl, thiazolyl, isoxazolyl, isothiazolyl, imidazolyl, pyrazolyl, oxadiazolyl, thiadiazolyl, triazolyl, tetrazolyl, pyridyl, pyrimidinyl, pyridazinyl, pyrazinyl, and pyranyl,
  and which optionally benzo-fused heterocycle is optionally substituted by up to three substituents independently selected from halogen, $C_{1-6}$ alkyl, $(C_n\text{-alkylene})CO_2H$, $(C_n\text{-alkylene})CO_2(C_{1-6}$ alkyl), $(C_n\text{-alkylene})CN$, $(C_n\text{-alkylene})CONR^5R^6$, $CH=CHCO_2H$, $CH=CHCONR^5R^6$, $CH=CHSO_2NR^5R^6$, $O(C_m\text{-alkylene})OH$, $CH_2NR^5R^6$, and $O(C_m\text{-alkylene})CONR^5R^6$;
  n is 0, 1 or 2;
  m is 1 or 2;
  and wherein the "C-alkylene" linking groups in the definitions above are optionally substituted by one or more $C_{1-6}$ alkyl;
  with the proviso that $R^1$, $R^2$ and $R^3$ are not all H;
  hereinafter referred to as "substances of the invention".
  "Alkyl" groups and the alkyl moiety of "alkoxy" groups can be straight-chain, branched or cyclic where the number of carbon atoms allows.
  "Halogen" means F, Cl, Br or I.
  The two definitions given for the $R^4$ moiety are of course tautomeric. The skilled man will realise that in certain circumstances one tautomer will prevail, and in other circumstances a mixture of tautomers will be present.

Pharmaceutically-acceptable salts are well know to those skilled in the art, and for example include those mentioned by Berge et al, in J. Pharm.Sci., 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more of the substituents on the compound of formula (I) contains an acidic moiety, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

The compounds of formula (I) having an acidic moiety can exist as one or more zwitterions. It is to be understood that all such zwitterions are included within the scope of the invention.

Certain of the compounds of the formula (I) may exist as geometric isomers. The compounds of the formula (I) may possess one or more asymmetric centres and so exist in two or more stereoisomeric forms. The present invention includes all the individual stereoisomers and geometric isomers of the substances of the invention and mixtures thereof.

Preferably $R^1$ is H, CN, halogen or methyl optionally substituted by one or more halogen.

More preferably $R^1$ is H, CN, Cl, Br or methyl.

Most preferably $R^1$ is Cl or Br.

Preferably $R^2$ is H, halogen, $C_{1-6}$ alkyl optionally substituted by one or more halogen, aryl. $CH_2OR^8$. $(C_n\text{-alkylene})$ $CONR^5R^6$, $CO_2H$ or $CH_2NR^5R^6$.

More preferably $R^2$ is H, Cl, methyl, phenyl, $CONHCH_2Ph$, $CH_2OPh$, $CH_2NCH_3Bn$, or pyrrolidinomethyl.

Most preferably $R^2$ is H.

Preferably $R^3$ is H, Cl, Br, $CF_3$, aryl, $(C_n\text{-alkylene})CO_2H$, $(C_n\text{-alkylene})CO_2(C_{1-6}$ alkyl), $(C_n\text{-alkylene})CONR^5R^6$, $CH=CHR^7$, $CH=CHCO_2H$, $CH=CHCONR^5R^6$, $CH=CHSO_2NR^5R^6$, $C=CR^7$, $O(C_m\text{-alkylene})OH$, $O(C_m\text{-alkylene})OR^8$, $OR^8$, $O(C_m\text{-alkylene})CONR^5R^6$, $CH_2OR^8$, or $CH_2NR^5R^6$.

More preferably $R^3$ is $CH=CHCO_2H$, (2-carboxypyrrolidino)$SO_2CH=CH$, (cyanophenyl)$CH=CH$, or (carboxyphenyl)$CH=CH$.

Yet more preferably $R^3$ is CH=CHCO$_2$H, (2-carboxypyrrolidino)SO$_2$CH=CH, (3-cyanophenyl)CH=CH, or (3-carboxyphenyl)CH=CH.

Most preferably $R^3$ is (2-carboxypyrrolidino)SO$_2$CH=CH, (3-cyanophenyl)CH=CH, or (3-carboxyphenyl)CH=CH.

A preferable group of substances of the invention are those wherein $R^1$ is H, CN, Cl, Br or methyl; $R^2$ is H, Cl, methyl, phenyl, CONHCH$_2$Ph, CH$_2$OPh, CH$_2$NCH$_3$Bn, or pyrrolidinomethyl; and $R^3$ is CH=CHCO$_2$H, (2-carboxypyrrolidino)SO$_2$CH=CH, (3-cyanophenyl)CH=CH, or (3-carboxyphenyl)CH=CH.

A yet more preferable group of substances of the invention are those in which $R_1$ is Cl or Br; $R^2$ is H; and $R^3$ is (2-carboxypyrrolidino)SO$_2$CH=CH, (3-cyanophenyl)CH=CH, or (3-carboxyphenyl)CH=CH.

A further preferred group of substances of the invention are those mentioned below in the Examples and the salts and solvates thereof.

Another aspect of the invention is a pharmaceutical composition comprising a substance of the invention according to the above definitions and a pharmaceutically-acceptable carrier.

Yet another aspect of the invention is a substance of the invention according to the above definitions for use as a medicament.

A further aspect of the invention is the use of a substance of the invention according to the above definitions, for the manufacture of a medicament for the treatment of a condition or process mediated by uPA, such as angiogenesis (neo-vascularization), bone restructuring, psoriasis, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis.

Yet another aspect of the invention is a method of treatment of a condition or process mediated by uPA, such as angiogenesis (neo-vascularization), bone restructuring, psoriasis, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis, comprising administering a therapeutic amount of a substance of the invention or composition according to the above definitions.

It is to be appreciated that reference to treatment includes prophylaxis as well as the alleviation of established detrimental symptoms of uPA-mediated conditions and processes, such that administration of the uPA inhibitor has a beneficial effect.

The substances of the invention may be separated and purified by conventional methods.

Separation of any diastereomeric mixtures may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The invention further provides Synthetic Methods for the production of substances of the invention, which are described below and in the Examples, in conjunction with the Preparations. The skilled man will appreciate that the substances of the invention could be made by methods other than those herein described, by adaptation of the methods herein described in the sections below and/or adaptation thereof, and of methods known in the art.

In the Synthetic Methods below, unless otherwise specified, the substituents are as defined above with reference to the compounds of formula (I) above.

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (1) and the desired acid or base, as appropriate. The salt may be precipitated from solution and collected by filtration, or may be collected by other means such as by evaporation of the solvent.

Synthetic Methods

Method 1

Compounds of formula (I) can be obtained from the corresponding 2-aminopyridine derivative (II) by reaction with cyanamide (NH$_2$CN) or a reagent which acts as a "NHC$^+$=NH" synthon such as carboxamidine derivatives, e.g. 1H-pyrazole-1-carboxamidine (M. S. Bernatowicz, Y. Wu, G. R. Matsueda, *J. Org. Chem.*, 1992, 57, 2497), the 3,5-dimethylpyrazole analogue thereof (M. A.Brimble et al, *J. Chem.Soc.Perkin Trans.I* (1990)31 1), simple O-alkylthiouronium salts or S-alkylisothiouronium salts such as O-methylisothiourea (F. El-Fehail et al, *J.Med.Chem.*(1986), 29, 984), S-methylisothiouronium sulphate (S.Botros et al, J.Med.Chem.(1986)29,874; P. S. Chauhan et al, *Ind. J. Chem.*, 1993, 32B, 858) or S-ethylisothiouronium bromide (M. L. Pedersen et al, *J.Org.Chem.*(1993) 58, 6966). Alternatively aminoiminomethanesulphinic acid, or aminoiminomethanesulphonic acid may be used (A. E. Miller et al, *Synthesis* (1986) 777; K. Kim et al, *Tet.Lett.*(1988) 29,3183).

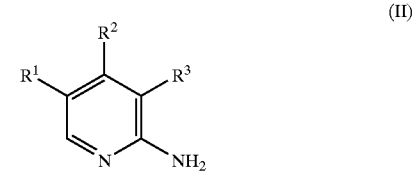

(II)

Other methods for this transformation are known to those skilled in the art (see for example, "Comprehensive Organic Functional Group Transformations", 1995, Pergamon Press, Vol 6 p639, T. L. Gilchrist (Ed.); Patai's "Chemistry of Functional Groups"Vol. 2. "The Chemistry of Amidines and Imidates"1991, 488).

2-Aminopyridines (II) may be prepared by standard published methods (see for example, "The Chemistry of Heterocyclic Compounds" Vol. 38 Pt. 2 John Wiley & Sons, Ed. F. G. Kathawala, G. M. Coppolq, H. F. Schuster) including, for example, by rearrangement from the corresponding carboxy-derivative (Hoffman, Curtius, Lossen, Schmidt-type rearrangements) and subsequent deprotection.

Alternatively, 2-aminopyridines may be prepared by direct displacement of a ring hydrogen using the Chichibabin reaction (A. F. Pozharskii et. al. *Russian Chem. Reviews*, 1978, 47, 1042. C. K. McGill et. al *Advances in Heterocyclic Chemistry* 1988, Vol. 44, 1)

2-Aminopyridines (II) may alternatively be prepared from the corresponding 2-halopyridines by direct displacement of a leaving group such as Cl or Br with a nitrogen nucleophile such as azide (followed by reduction), or by ammonia, or through Pd-catalysis with a suitable amine (such as benzylamine) followed by deprotection using standard conditions well-known in the art. Examples of such chemistry is outlined in "The Chemistry of Heterocyclic Compounds" Vol. 14, Pts. 2 and 3 John Wiley & Sons, in particular Pt. 2, (1961), Pt. 3 (1962), Pt. 2- supplement (1974) and Pt. 3-supplement (1974).

2-Halopyridines may be prepared by methods well known in the literature. For example, by treatment of 2-hydroxypyridines (2-pyrimidinones) with halogenating agents such as $SOCl_2$ (Y. S. Lo. Et. *Al. Syn. Comm.*, 1988, 19, 553), $POCl_3$ (M. A. Walters, *Syn. Comm.*, 1992, 22, 2829), or $POBr_3$ (G. J. Quallich, *J. Org. Chem.*, 1992, 57, 761). Alternatively, 2-alkoxypyridines may be transformed to the corresponding 2-aminopyridines under Vilsmeir-Haack conditions such as $POCl_3+DMF$ (L-L Lai et. *Al. J Chem. Res.* (S), 1996, 194). The corresponding N-oxide may be treated with suitable halogenating reactions to directly produce 2-halopyridines—e.g. $POCl_3/PCl_5$ (M. A. Walters, *Tetrahedron Lett.*, 1995, 42, 7575). Direct halogenation of the 2-position is possible in the presence of certain ring substituents (M. Tiecco et. al. Tetrahedron, 1986, 42, 1475, K. J. Edgar, *J. Org Chem.*, 1990, 55, 5287).

Method 2

Compounds of formula (I) can be obtained from the corresponding 2-aminopyridine derivative (II) as defined in Method 1 above, via reaction with a reagent which acts as a protected amidine(2+) synthon (III):

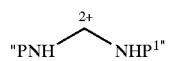

such as a compound $PNHC(=Z)NHP^1$, $PN=CZ^1NHP^1$ or $PNHCZ^1=NP_1$, where Z is a group such as O. or S and $Z^1$ is a leaving group such as Cl, Br, I, mesylate. tosylate, alkyloxy, etc., and where P and $P^1$ may be the same or different and are N-protecting groups such as are well-known in the art, such as t-butoxycarbonyl, benzyloxycarbonyl, arylsulphonyl such as toluenesulphonyl, nitro, etc.

Examples of reagents that act as synthons (III) include N, N'-protected-S-alkylthiouronium derivatives such as N, N'-bis(t-butoxycarbonyl)-S-Me-isothiourea, N, N'-bis (benzyloxycarbonyl)-S-methylisothiourea, or sulphonic acid derivatives of these (*J. Org. Chem.* 1986, 51, 1882), or S-arylthiouronium derivatives such as N, N'-bis(t-butoxycarbonyl)-S-(2,4-dinitrobenzene) (S. G. Lammin, B. L. Pedgrift, A. J. Ratcliffe, *Tet. Lett.* 1996, 37, 6815), or mono-protected analogues such as [(4-methoxy-2,3,6-trimethylphenyl)sulphonyl]-carbamimidothioic acid methyl ester or the corresponding 2,2,5,7,8-pentamethylchroman-6-sulphonyl analogue (D. R. Kent, W. L. Cody, A. M. Doherty, *Tet. Lett.*, 1996, 37, 8711), or S-methyl-N-nitroisothiourea (L. Fishbein et al, *J.Am. Chem.Soc.* (1954) 76, 1877) or various substituted thioureas such as N, N'-bis (t-butoxycarbonyl)thiourea (C. Levallet, J. Lerpiniere, S. Y. Ko, *Tet.* 1997, 53, 5291) with or without the presence of a promoter such as a Mukaiyama'reagent (Yong, Y. F.; Kowalski, J. A.; Lipton, M. A. *J. Org. Chem.*, 1997, 62, 1540), or copper, mercury or silver salts, particularly with mercury (II) chloride. Suitably N-protected O-alkylisoureas may also be used such as O-methyl-N-nitroisourea (N. Heyboer et al, *Rec.Chim. Trav.Pays-Bas* (1962)81,69). Alternatively other guanylation agents known to those skilled in the art such as 1-H-pyrazole-1-[N,N'-bis(t-butoxycarbonyl)]carboxamidine, the corresponding bis-Cbz derivative (M. S. Bernatowicz, Y. Wu, G. R. Matsueda, *Tet. Lett.* 1993, 34, 3389) or mono-Boc or mono-Cbz derivatives may be used (B. Drake. *Synthesis,* 1994, 579, M. S. Bernatowicz.. *Tet. Lett.* 1993, 34, 3389). Similarly, 3,5-dimethyl-1-nitroguanylpyrazole may be used (T. Wakayima et al, *Tet.Lett.*(1986)29,2143).

The reaction can conveniently be carried out using a suitable solvent such as dichloromethane, N,N-dimethylformamide (DMF), methanol.

The reaction is also conveniently carried out by adding mercury (II) chloride to a mixture of the aminopyridine (II) and a thiourea derivative of type (III) in a suitable base/solvent mixture such as triethylamine/dichloromethane.

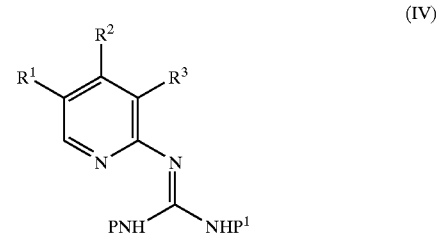

The product of this reaction is the protected pyridinylguanidine (IV), which can conveniently be deprotected to give (I) or a salt thereof. For example, if the protecting group P and/or $P^1$ is t-butoxycarbonyl, conveniently the deprotection is carried out using an acid such as trifluoroacetic acid (TFA) or hydrochloric acid, in a suitable solvent such as dichloromethane, to give a trifluoroacetate (triflate) salt of (I), either as the mono- or ditriflate.

If P and/or $P^1$ is a hydrogenolysable group, such as benzyloxycarbonyl, the deprotection could be performed by hydrogenolysis.

Other protection / deprotection regimes include:

nitro (K. Suzuki et al, *Chem.Pharm.Bull.* (1985)33,1528, Nencioni et al, *J.Med.Chem.*(1991)34,3373, B. T. Golding et al, *J.C.S.Chem.Comm.*(1994)2613;

p-toluenesulphonyl (J. F. Callaghan et al, *Tetrahedron* (1993) 49 3479;

mesitylsulphonyl (Shiori et al, *Chem.Pharm.Bull.*(1987) 35,2698, ibid.(1987)35,2561, ibid., (1989)37,3432, ibid., (1987)35,3880, ibid., (1987)35,1076;

2-adamantoyloxycarbonyl (Iuchi et al, *ibid.,* (1987) 35, 4307; and methylsulphonylethoxycarbonyl (Filippov et al, *Syn.Lett.* (1994)922)

It will be apparent to those skilled in the art that other protection and subsequent deprotection regimes during synthesis of a compound of the invention may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

Method 3

Compounds with the formula (I) can be obtained from compounds of formula (V):

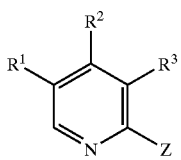

(V)

where Z is a suitable leaving group such as Cl, Br or OPh, by displacement of the leaving group by the free base of guanidine.

The free base of guanidine may conveniently be generated in situ from a suitable salt, such as the hydrochloride, carbonate, nitrate, or sulphate with a suitable base such as sodium hydride, potassium hydride, or another alkali metal base, preferably in a dry non-protic solvent such as tetrahydrofuran (TBF), DMSO, N,N-dimethylformamide (DMF), ethylene glycol dimethyl ether (DME), N,N-dimethyl acetamide (DMA), toluene or mixtures thereof. Alternatively it can be generated from a suitable salt using an alkoxide in an alcohol solvent such as potassium t-butoxide in t-butanol, or in a non-protic solvent as above.

The thus formed free guanidine can be combined with the compound of formula (V) and the reaction to form compounds of formula (I) can be carried out at from room temperature to 200° C., preferably from about 50° C. to 150° C., preferably for between 4 hours and 6 days.

Method 4

Compounds of the formula (I) when one or more of $R^{1-3}$ contains a hydroxy group, may be prepared from a suitably "protected" hydroxy derivative, i.e. a compound of the formula (I) where one or more of $R^{1-3}$ contains a corresponding "$OP^1$" where $P^2$ is a suitable O-protecting group such as O-benzyl. The benzyl group may be removed for example by catalytic hydrogenation using a palladium on charcoal catalyst in a suitable solvent such as ethanol at about 20° C. and elevated pressure, optionally in the presence of an excess of an acid such as HCl or AcOH, or TFA, or by other known deprotection methods.

Suitable O-protecting groups and protection/deprotection can be found in the texts by Greene and Wuts, and Kocienski, supra.

Method 5

Compounds of the invention where $R^2$ or $R^3$ is or contains a carboxylic acid group or carbamoyl group can be made from the corresponding compound where the substituent is or contains a nitrile by full or partial hydrolysis. Compounds of the invention where $R^2$ or $R^3$ is or contains a carboxylic acid group can be made from the corresponding compound where the substituent is a carbamoyl moiety, by hydrolysis. The hydrolysis can be carried out by methods well-known in the art, for example those mentioned in "Advanced Organic Chemistry" by J. March, 3rd edition (Wiley-Interscience) chapter 6–5, and references therein. Conveniently the hydrolysis is carried out using concentrated hydrochloric acid, at elevated temperatures, and the product forms the hydrochloride salt.

Compounds of the formula (I) where one or more of $R^1$, $R^2$ or $R^3$ is or contains Cl or Br may be dehalogenated to give the corresponding hydrido compounds of formula (I) by hydrogenolysis, suitably using a palladium on charcoal catalyst, in a suitable solvent such as ethanol at about 20° C. and at elevated pressure.

Compounds of formula (I) in which one or more of $R^2$ or $R^3$ contains an amide moiety may be made via reaction of an optionally protected corresponding carboxy compound, by coupling with the amine of choice, e.g. via initial formation of the corresponding acid halide or mixed anhydride, and subsequent reaction with the amine, followed by deprotection if appropriate. Such transformations are well-known in the art.

Certain of the compounds of formula (I) which have an electrophilic group attached to an aromatic ring may be made by reaction of the corresponding hydrido compound with an electrophilic reagent. For example sulphonylation of the aromatic ring using standard reagents and methods, such as fuming sulphuric acid, gives a corresponding sulphonic acid. This can then be optionally converted into the corresponding sulphonamide by methods known in the art, for example by firstly converting to the acid chloride followed by reaction with an amine.

Certain of the substances of the invention can be made via cross-coupling techniques such as by reaction of a compound containing a bromo-substituent attached to e.g. an aromatic ring, with e.g. a boronic acid derivative, an olefin or a tin derivative by methods well-known in the art, for example by the methods described in certain of the Preparations below.

Certain of the substances of the invention having an electrophilic substituent can be made via halogen/metal exchange followed be reaction with an electrophilic reagent. For example a bromo-substituent may react with a lithiating reagent such as n-butyllithium and subsequently an electrophilic reagent such as $CO_2$, an aldehyde or ketone, to give respectively an acid or an alcohol.

Substances of the invention are available by either the methods described herein in the Methods and Examples or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a compound of the invention. This may be achieved by conventional techniques, for example as described in "Protective Groups in Organic Synthesis" by T W Greene and P G M Wuts, John Wiley and Sons Inc. (1999), and by P. J. Kocienski, in "Protecting Groups"Georg Thieme Verlag (1994).

For human use, the substances of the invention can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution or suspension which may contain other substances, for example, enough salt or glucose to make the solution isotonic with blood. They can be administered topically, in the form of sterile creams, gels, suspensions, lotions, ointments, dusting powders, sprays, drug-incorporated dressings or via a skin patch. For example they can be incorporated into a cream consisting of an aqueous or oily emulsion of polyethylene glycols or liquid paraffin, or they can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. The compound or salt could also be administered intraocularly as an eye drop with appropriate buffers, viscosity modifiers (e.g. cellulose derivatives), preservatives (e.g. benzalkonium chloride (BZK)) and agents to adjust tenicity (e.g. sodium chloride). All such formulations may also contain appropriate stabilisers and preservatives. For oral and parenteral administration to human patients, the daily dosage level of the substances of the invention will be from 0.001 to 20, preferably from 0.01 to 20, more preferably from 0.1 to 10, and most preferably from 0.5 to 5 mg/kg (in single or divided doses). Thus tablets or capsules of the substances of the invention will contain from 0.1 to 500, preferably from 50 to 200, mg of active substance for administration singly or two or more at a time as appropriate.

The physician in any event will determine the actual dosage which will be most suitable for an individual patient and it will vary with the age, weight and response of the particular patient. The above dosages are exemplary of the average case; there can of course be individual instances where higher or lower dosage ranges are merited, and such are within the scope of this invention.

It is to be appreciated that reference to treatment includes prophylaxis as well as the alleviation of established symptoms of the condition to be treated.

Test Methods

Substances were tested for their ability to inhibit human urokinase, human tPA and human plasmin, using substantially the same methods as described by Yang, et al, *J.Med. Chem.*,(1990)33,2961. The urokinase assay was carried out using S-2444 (Quadratech 820357) as substrate and the urokinase used was HMWT Human Urokinase (Calbiochem 672081). The tPA assay was carried out using S-2288 (Quadratech 820832) tPA substrate, Quadratech 321116 as tPA stimulator, and the tPA used was Human tPA (Quadratech 881157). The plasmin assay was carried out using human plasmin (Quadratech 810665) acting on Chromozym-PL (Boehringer 378461) as substrate.

EXAMPLES AND PREPARATIONS

Melting points were determined using a Gallenkamp melting point apparatus and are uncorrected. Nuclear magnetic resonance data were obtained using a Varian Unity 300 or Varian Inova 400 spectrometer, and are quoted in parts per million from tetramethylsilane. Mass spectral data were obtained on a Finnigan Mat. TSQ 7000 or a Fisons Instruments Trio 1000. The calculated and observed ions quoted refer to the isotopic composition of lowest mass. Reference to "ether" in this section should be read as diethyl ether, unless specified otherwise. "Ph" represents the phenyl group. "Bn" represents the benzyl group. "Me" represents the methyl group. "TLC" means thin layer chromatography. "RT" means room temperature. "EtOAc" means ethyl acetate. Other abbreviations are standard and well-known in the art. Nomenclature has been allocated using the IUPAC NamePro software available from Advanced Chemical Development Inc.

Example 1

N"-(5-Methyl-2-pyridinyl)guanidine (I: $R^1$=CH$_3$; $R^2$=$R^3$=H)

Trifluoroacetic acid (2 ml) was added with care to tert-butyl N-[(tert-butoxycarbonyl)amino][(5-methyl-2-pyridinyl)imino]methylcarbamate (111 mg, 0.32 mmol) and the solution stirred at RT for 2 h, diluted with toluene and evaporated to dryness. The solid was azeotroped with methylene chloride, and recrystallised from methanol to give the trifluoroacetic acid salt of N"-(5-methyl-2-pyridinyl)guanidine as a cream-coloured solid (32 mg, 0.1 mmol):

$^1$H (δ, d$_6$-DMSO, 300 MHz); 2.2 (3H, s), 6.95 (1H, d), 7.7 (1H, d), 8.1 (1H, s), 8.35 (4H, br s), 1105 (1H, br s);

LRMS 151 (MH).

Other compounds of formula (I; R4 is N=C(NH2)2) prepared by the same method are listed in Table 1 below.

TABLE 1

NB all as trifluoroacetic acid salts unless noted otherwise

| Example | R³ | R² | R¹ | Mp ° C. | Elemental Analysis | LRMS | ¹H, δ |
|---|---|---|---|---|---|---|---|
| 2 | H | H | Cl | — | Found: C, 32.46; H, 2.87; N, 18.08 Calcd for $C_8H_7ClN.CF_3CO_2H + 0.25$ $CH_2Cl_2$,C, 32.40; H, 2.80; N, 18.32 | — | (DMSO-$d_6$, 300MHz) 7.1(1H, d), 8.0 (1H, dd), 8.1–8.4(5H, br m) |
| 3 | H | H | Br | — | — | 215, 217 (MH) | (DMSO-$d_6$, 300MHz) 7.0(1H, dd), 8.05 (1H, dd), 8.3(4H, br s), 8.4(1H, d), 11.4(1H, br s) |
| 4 | H | Ph | H | 156–8 | Found: C, 51.39; H, 3.96; N, 17.06. Calcd for $C_{12}H_{12}N_4.CF_3CO_2H$: C, 51.53; H, 4.02; N, 17.17 | 213(MH) | (DMSO-$d_6$, 300MHz) 7.25(1H, s), 7.45–7.6(4H, m), 7.75(2H, d), 8.25(2H, br s), 8.35 (2H, d), 11.4(1H, br s) |
| 5 | H | CONHCH₂Ph | H | — | — | 270(MH), 539 ($M_2H$) | (DMSO-$d_6$, 300MHz) 4.5(2H, d), 7.2–7.35 (4H, m), 7.4(1H, s), 7.6(1H, d), 8.3(4H, br s), 8.4(1H,d), 9.4(1H, dd), 11.1(1H, br s) |
| 6 | Cl | H | Cl | — | — | 205, 207(MH) | (DMSO-$d_6$, 300MHz) 8.35(1H, d), 8.5(5H, br s), 9.9(1H, s) |
| 7(a) | Br | H | Cl | — | Found: C, 24.84; H, 2.39; N, 18.67. Calcd for $C_8H_6BrClN_4.HCl + 0.1 CH_2Cl_2$ C, 24.88; H, 2.46; N, 19.03 | 249, 251, 253 (MH) | (DMSO-$d_6$, 300MHz) 8.4(1H, s), 8.2–8.8(5H, br s), 9.8(1H, s) |
| 8 | Cl | H | Br | — | — | 249, 251, 253 (MH) | ($CF_3CO_2D$, 300MHz) 8.05(1H, s), 8.35(1H, s), 11.45(5H, s) |
| 9 | E-CH=CHCO₂H | H | Cl | 207–9 | Found: C, 37.2; H, 2.86; N, 15.32. Calcd for $C_8H_9ClN_4O_2.CF_3CO_2H + 0.05$ $H_2O$. C, 37.54; H, 2.95; N, 15.63 | 241, 243(MH) | ($CF_3CO_2D$, 300MHz) 6.65(1H, d), 8.05(1H, s), 8.35(1H, s), 11.45(6H, br s) |
| 10 | CH₂CH₂CO₂H | H | Cl | 154–6 | Found: C, 37.15; H, 3.37; N, 15.56. Calcd for $C_9H_{11}ClN_4O_2.CF_3CO_2H$: C, 37.04; H, 3.39; N, 15.71 | 243, 245(MH) | ($CF_3CO_2D$, 300MHz) 1.5–3.3(2H, m), 3.3–3.4 (2H, m), 8.15(1H, s), 8.55(1H, s) |
| 11 | E-CH=CHCONHMe | H | Cl | 208–210 | — | 254, 256(MH); 507, 509($M_2H$) | (DMSO-$d_6$, 300MHz) 2.7(3H, d), 6.7(1H, d), 7.5(1H, d), 8.0–8.3(6H, m), 8.4(1H, d), 9.8 (1H, br s) |
| 12 | E-CH=CHCONHCH₂Ph | H | Cl | — | Found: C, 48.53, H, 3.88; N, 15.29. Calcd for $C_{16}H_{16}ClN_5O.CF_3CO_2H + 0.05$ $H_2O$. C, 48.85; H, 3.94; N, 15.65 | 330, 332(MH) | (DMSO-$d_6$, 300MHz) 4.4(2H, d), 6.8(1H, d), 7.2–7.35(5H, m), 7.6(1H, d), 8.2(1H, d), 8.2–8.35(4H, br s), 8.4(1H, d), 8.7(1H, t), 9.95 (1H, s) |
| 13 | E-CH=CHCO-(3-hydroxypiperidino) | H | Cl | — | Found: C, 42.79; H, 4.35; N, 14.64. Calcd for $C_{14}H_{28}ClN_5O_2 + 1.25 CF_3CO_2H$: C, 42.50; H, 4.16; N, 15.02 | 324, 326(MH) | (DMSO-$d_6$ + 1 drop $CF_3CO_2D$, 400MHz) 1.1–1.55(2H, m), 1.6–1.95(2H, m), 2.75(0.5H, dd), 3.1–3.2(0.5H, m), 3.3–3.45(1.5H, m), 3.5–3.65(1H, m), 3.8(0.5H, dd), 3.95(0.5H, d), 4.4(0.5H, dd), 7.45(1H, dd), 7.6(1H, d), 8.2 (1H, br s), 8.35(1H, s), 8.5(1H, d) |
| 14 | E-CH=CHCON(Me)C | H | Cl | 148–150 | Found: 49.27; H, 4.10; N, 15.00. Calcd for | 344, 346(MH) | (DMSO-$d_6$, 300MHz) 2.9 & 3.15(3H, both s), 4.6 & 4.85(2H, both s), 7.1–7.4(5H, m), 7.5 |

TABLE 1-continued

NB all as trifluoroacetic acid salts unless noted otherwise

| Example | R³ | R² | R¹ | Mp °C. | Elemental Analysis | LRMS | ¹H, δ |
|---|---|---|---|---|---|---|---|
| 15 | H₂Ph₂ | | | | C₁₇H₅ClN₅O.CF₃CO₂H + 0.25 H₂O: C, 49.35; H, 4.25; N, 15.14 | | (1H, app. dd), 7.65(1H, app. dd), 8.0–8.2(3H, m), 8.35(1H, app. dd), 8.55(1H, app. dd), 9.9 (1H, br s) |
| 15 | E-CH=CHCO(morpholino) | H | Cl | — | Found: C, 41.40; H, 4.03; N, 15.36. Calcd for C₁₃H₁₆ClN₅O₂ + 1.5 CF₃CO₂H: C, 41.15; H, 3.84; N, 15.48 | 310, 312(MH) | (DMSO-d₆, 300MHz) 3.55–3.8(8H, br m), 7.45(1H, d), 7.6(1H, d), 8.1–8.25(4H, br s), 8.4(1H, d), 8.55(1H, d), 9.95(1H, br s) |
| 16 | E-CH=CHSO₂NHMe | H | Cl | — | — | 290, 292(MH) | (DMSO-d₆, 300MHz) 2.55(3H, d), 7.3(1H, q) 7.4(2H, s), 8.0–8.2(4H, br m) 8.45(1H, d), 8.5(1H, d), 10.0–10.15(1H, m), |
| 17 | E-CH=CHPh | H | Cl | >275 | Found: C, 49.55; H, 3.62; N, 14.27. Calcd for C₁₄H₁₃ClN₄.CF₃CO₂H: C, 49.38; H, 3.65; N, 14.49 | 273(MH) | (DMSO-d₆, 300MHz) 7.2–7.5(5H, m), 7.65 (2H, d), 8.1–8.35(5H, m), 8.35(1H, s), 10.0 (1H, s) |
| 18 | E-CH=CH(4-MeOC₆H₄) | H | Cl | >275 | Found: C, 49.04; H, 3.81; N, 13.09. Calcd for C₁₅H₁₅ClN₄O.CF₃CO₂H: C, 48.99; H, 3.87; N, 13.44 | 303, 305(MH) | (DMSO-d₆, 300MHz) 3.8(3H, s), 7.0(2H, d), 7.05(1H, d), 7.4(1H, d), 7.6(2H, d), 8.1–8.3 (5H, m), 9.9(1H, br s) |
| 19⁽ᵇ⁾ | E-CH=CH(2-pyridyl) | H | Cl | — | Found: C, 41.87; H, 3.05; N, 14.75. Calcd for C₁₃H₁₂ClN₅ + 1.75 CF₃CO₂H: C, 41.87; H, 2.93; N, 14.80 | 274, 276(MH); 547, 549(M₂H) | (DMSO-d₆, 300MHz) 7.3–7.4(1H, m), 7.4–7.5 (2H, m), 7.75(1H, d), 7.8–7.9(1H, m), 8.1–8.3 (4H, br m), 8.35(1H, d), 8.45(1H, d), 8.6–8.65 (1H, m), 10.0(1H, s) |
| 20 | E-CH=CH-cyclohexyl | H | Cl | 156–158 | — | 279, 281(MH) | (DMSO-d₆, 400MHz) 1.1–1.35(5H, m), 1.6–1.65(1H, m), 1.65–1.84(4H, m), 2.1–2.2(1H, m) 6.45(2H, s), 8.1(1H, br s), 8.15–8.25(3H, br s), 8.25(1H, s), 9.0(1H, s), 9.7(1H, br s) |
| 21 | E-CH=CH-(3,4-methylenedioxyphenyl) | H | Cl | — | Found: C, 45.96; H, 3.17; N, 12.65. Calcd for C₁₅H₁₃ClN₄O₂ + 1.2 CF₃CO₂H: C, 46.03; H, 3.16; N, 12.35 | 317(MH) | (DMSO-d₆, 400MHz) 6.05(2H, s), 6.95(1H, d), 7.05–7.15(2H, m), 7.3(1H, s), 7.4(1H, d), 8.1–8.3(6H, m), 9.85(1H, br s) |
| 22 | E-CH=CH(3-CN-(C₆H₄)) | H | Cl | — | Found: C, 49.00; H, 3.35; N, 16.58. Calcd for C₁₅H₁₂ClN₅.CF₃CO₂H + 0.25 H₂O: C, 49.05; H, 3.27; N, 16.82 | 298, 300(MH) | (CF₃CO₂D, 400MHz) 7.1(1H, d), 7.2(1H, d), 7.45–7.55(1H, m), 7.6(1H, d), 7.75–7.8(2H, m), 8.2(1H, s), 8.3(1H, s), 11.4(5H, s) |
| 23 | C≡CPh | H | Cl | 179–181 | Found: C, 49.76; H, 3.21; N, 14.25. Calcd for C₁₄H₁₁ClN₄.CF₃CO₂H: C, 49.94; H, 3.14; N, 14.56 | 271, 273(MH) | (DMSO-d₆, 400MHz) 7.45–7.5(3H, m), 7.55–7.7(2H, m), 8.3(1H, d), 8.4(1H, d), 8.3–8.6 (4H, br s), 9.8(1H, br s) |
| 24 | OPh | H | Cl | 170–172 | Found: C, 44.61; H, 3.15; N, 14.58. Calcd for C₁₂H₁₁ClN₄O.CF₃CO₂H: C, 44.63; H, 3.19; N, 14.87 | 263, 265(MH) | (DMSO-d₆, 400MHz) 7.2(2H, d), 7.3(2H, d), 7.5–7.6(2H, m), 8.1(1H, s), 8.2–8.5(4H, br s), 10.1(1H, s) |
| 25 | OCH₂Ph | H | Cl | 176–8 | Found: C, 45.73; H, 3.57; N, 13.68. Calcd for C₁₃H₁₃ClN₄O.CF₃CO₂H + 0.5 H₂O + 0.05 EtOAc: C, 45.76; H, 3.79; N, 14.04 | 277, 279(MH) | (DMSO-d₆, 400MHz) 5.35(2H, s), 7.3–7.45 (3H, m), 7.45–7.5(2H, m), 7.8(1H, s), 7.9 (1H, s), 8.0–8.7(4H, br s), 9.7(1H, s) |

TABLE 1-continued

NB all as trifluoroacetic acid salts unless noted otherwise

| Example | $R^3$ | $R^2$ | $R^1$ | Mp °C. | Elemental Analysis | LRMS | $^1H$, δ |
|---|---|---|---|---|---|---|---|
| 26 | $OCH_2CH_2OH$ | H | Cl | 169–171 | Found: C, 34.63; H, 3.46; N, 15.76. Calcd for $C_8H_{11}ClN_5O_2.CF_3CO_2H + 0.25 H_2O$: C, 34.39; H, 3.61; N, 16.05 | 231, 233(MH) | (DMSO-$d_6$, 400MHz) 3.75(2H, s), 4.2(2H, s), 4.95(1H, s), 7.75(1H, s), 7.9(1H, s), 8.0–8.6(4H, br s), 9.7(1H, s) |
| 27 | $OCH_2CH_2OMe$ | H | Cl | 120–122 | Found: C, 36.75; H, 3.87; N, 15.18. Calcd for $C_9H_{13}ClN_5O_2.CF_3CO_2H + 0.2 H_2O$: C, 36.47; H, 4.01; N, 15.46 | 245, 247(MH) | (DMSO-$d_6$, 300MHz) 3.25(3H, s-under water peak by $CF_3CO_2D$ exchange), 3.7 (2H, t), 4.35(2H, t), 7.75(1H, d), 7.9(1H, d), 8.1–8.7(4H, br s), 9.7(1H, s) |
| 28 | $OCH_2CONCH_2Ph$ | H | Cl | 209–211 | Found: C, 45.23; H, 3.80; N, 15.23. Calcd for $C_{15}H_{16}ClN_5O_2.CF_3CO_2H$: C, 45.60; H, 3.83; N, 15.64 | 334, 336(MH) | ($CF_3CO_2D$, 400MHz) 4.35(2H, s), 4.9(2H, s), 7.15–7.2(2H, m), 7.2–7.3(3H, m), 7.35 (1H, s), 7.95(1H, s) |
| 29 | $OCH_2(3-CO_2Me\text{—}C_6H_4)$ | H | Cl | 187–188.5 | Found: C, 45.26; H, 3.54; N, 12.29. Calcd for $C_{15}H_{15}ClN_4O_3.CF_3CO_2H$: C, 45.50; H, 3.59; N, 12.48 | 335, 337(MH) | ($CF_3CO_2D$, 400MHz) 4.0(3H, s), 5.2 (2H, s), 7.4(1H, s), 7.5(1H, t), 7.6(1H, d), 7.85(1H, s), 8.1–8.05(2H, m) |
| 30 | $CH_2OPh$ | H | Cl | 177–180 | Found: C, 44.60; H, 3.60; N, 14.03. Calcd for $C_{13}H_{13}ClN_4O.CF_3CO_2H + 0.5 H_2O$: C, 45.07; H, 3.78; N, 14.02 | 277, 279 (MH) | (DMSO-$d_6$, 300MHz) 5.15(2H, s), 7.0(1H, t), 7.05(2H, d), 7.3(2H, dd), 8.1(1H, d), 8.2–8.4(5H, m), 9.6(1H, br s) |
| 31 | Cl | Cl | Cl | 210.5–212.5 | Found: C, 27.36; H, 1.71; N, 15.45. Calcd for $C_8H_6Cl_3F_3N_4O_2 + 1.05 CF_3CO_2H$: C, 27.08; H, 1.70; N, 15.60 | 239, 241, 243, 245(MH) | (DMSO-$d_6$, 300MHz) 8.3(4H, br s), 8.5 (1H, s), 10.0(1H, br s) |
| 32 | Me | Cl | Cl | 201–3 | Found: C, 32.10; H, 2.75; N, 16.74. Calcd for $C_7H_8Cl_2N_4.CF_3CO_2H$: C, 32.45; H, 2.72; N, 16.82 | 219, 221, 223 (MH) | (DMSO-$d_6$, 300MHz) 8.3(1H, s), 8.5(3H, br s), 9.85(1H, br s) |
| 33 | $CH_2OPh$ | Cl | Cl | 164–166 | Found: C, 42.10; H, 3.04; N, 13.03. Calcd for $C_{13}H_{12}Cl_2N_4.CF_3CO_2H$: C, 42.38; H, 3.08; N, 13.18 | 311, 313(MH) | (DMSO-$d_6$, 300MHz) 5.25(2H, s), 6.95–7.05(3H, m), 7.25–7.35(2H, m), 8.3–8.5 (5H, br m), 10.0(1H, br s) |
| 34[c] | $CH_2NMe Bn$ | Cl | Cl | 202–5 | Found: C, 40.07; H, 3.27; N, 12.19. Calcd for $C_{15}H_{17}Cl_2N_5.2CF_3CO_2H$: C, 40.29; H, 3.38; N, 12.37 | 338, 339, 341 (MH) | (DMSO-$d_6$ + 1 drop of $CF_3CO_2D$, 300 MHz) 2.8(3H, s), 4.4–4.55(4H, m), 7.4–7.5 (3H, m), 7.55–7.6(2H, m), 8.4(1H, s) |
| 35[c] | $CH_2N(CH_2)_4$ | Cl | Cl | 161–3 | Found: C, 34.67; H, 3.28; N, 13.33. Calcd for $C_{11}H_{15}Cl_2N_5.2CF_3CO_2H$: C, 34.90; H, 3.32; N, 13.57 | 288, 290, 292 (MH) | ($CF_3CO_2D$, 400MHz) 2.0–2.1(2H, m), 2.1–2.3(2H, m), 3.25–3.35(2H, m), 3.65–3.75 (2H, m), 4.65(2H, s), 8.3(1H, s) |

[a]HCl salt
[b]appeared to be mixture of mono- and bis-triflate salt
[c]bis-TFA salt

Example 36

3-((E)-2-{5-Chloro-2-[(diaminomethylene)amino]-3-pyridinyl}ethenyl)benzoic Acid (I: $R^1$=Cl; $R^2$=H; $R^3$=E—CH=CH(3-$C_6H_4$—$CO_2H$)

N"-5-chloro-3-[(E)-2-(3-cyanophenyl)ethenyl]-2-pyridinylguanidine (85 mg, 0.2 mmol) was heated to reflux in conc. HCl (1.5 ml) and acetic acid (0.5 ml) for 48 h. Solvent was removed in vacuo and the residue azeotropically dried with toluene to give a light brown solid which was triturated with diethyl ether to give 3-((E)-2-{5-chloro-2-[(diaminomethylene)amino]-3-pyridinyl}ethenyl)benzoic acid as an off-white solid (65 mg, 0.2 mmol):

$^1$H ($\delta$, $CF_3CO_2D$, 400 MHz) 7.2 (1H, d), 7.4 (1H, d), 7.5 (1H, t), 7.8 (1H, d), 8.1 (1H, d), 8.3 (1H, s), 8.45 (1H, s), 8.55 (1H, s);

LRMS 317, 319 (MH);

M. Pt. >275° C.;

El. Anal.—Found: C, 49.36; H, 4.24; N, 15.51. Calcd for $C_{15}H_{13}ClN_4O_2 \cdot HCl + 2/3$ water: C, 49.35; H, 4.23; N, 15.35.

Preparation 1 t-Butyl (E)-3-(2-amino-5-chloro-3-pyridinyl)-2-propenoate

A mixture of 3-bromo-5-chloro-2-pyridinamine (C. W. Murtiashaw, R. Breitenbach, S. W. Goldstein, S. L. Pezzullo, J. Quallich, R. Sarges, *J. Org. Chem.*, 1992, 57, 1930) (8.56 g, 41.4 mmol), t-butyl acrylate (12 ml, 82 mmol), tri-o-tolylphosphine (2.92 g. 9.6 mmol) and palladium acetate (540 mg, 2.4 mmol) in triethylamine (130 ml) was heated in a sealed bomb to 150° C. for 10 hours. The reaction mixture was filtered, the residue washed with EtOAc and the combined filtrates evaporated to a dark brown oil. Purification by column chromatography upon silica gel using hexane—EtOAc (7:3) as eluant and subsequent crystallisation from hexane at −78° C. gave the title compound as a bright yellow solid (4.75 g, 18.6 mmol).

$^1$H ($\delta$, $CDCl_3$, 300 MHz) 1.5 (9H, s), 4.7 (2H, br s), 6.3 (1H, d), 7.45 (1H, d), 7.55 (1H, s), 8.0 (1H, s);

LRMS 255, 257 (MH);

El. Anal.—Found: C, 56.55; H, 5.94; N, 10.91. Calcd for $C_{12}H_{15}ClN_2O_2$: C, 56.58; H, 5.94; N, 10.99.

Preparation 2

(E)-3-(2-Amino-5-chloro-3-pyridinyl)-2-propenoic Acid t-Butyl (E)-3-(2-amino-5-chloro-3-pyridinyl)-2-propenoate (2 g, 7.8 mmol), was stirred in 3 ml of trifluoroacetic acid at ambient temperature for 1 hour. The reaction mixture was diluted with toluene, evaporated to dryness, and the residue triturated with diethyl ether to yield the title compound as a pale yellow solid (1.89 g, 6.0 mmol).

$^1$H ($\delta$, $d_6$-DMSO, 300 MHz) 5.0–7.5 (br s), 6.5 (1H, d), 7.65 (1H, d), 7.95 (1H ,s), 8.0 (1H, s);

LRMS 199, 201 (MH);

El. Anal.—Found: C, 38.41; H, 2.49; N, 8.87. Calcd for $C_8H_7ClN_2O_2 \cdot CF_3CO_2H$: C, 38.42; H, 2.58; N, 8.96.

Preparation 3 t-Butyl 3-(2-amino-5-chloro-3-pyridinyl)propanoate

To a solution of t-butyl (E)-3-(2-amino-5-chloro-3-pyridinyl)-2-propenoate (500 mg, 2.0 mmol) in ethanol (10 ml) at RT was added sodium borohydride (317 mg, 8.4 mmol) portionwise and the mixture stirred for 16 h. After the addition of water, the ethanol removed in vacuo and the mixture extracted with diethyl ether. The ethereal extracts were dried over $MgSO_4$, evaporated to dryness and purified by column chromatography upon silica gel using hexane—EtOAc (7:3) as eluant to give t-butyl 3-(2-amino-5-chloro-3-pyridinyl)propanoate as a colourless oil (340 mg, 1.3 mmol).

$^1$H ($\delta$, $CDCl_3$, 300 MHz) 1.4 (9H, s), 2.5 (2H, t), 2.7 (2H, t), 4.6 (2H, br s), 7.2 (1H, d), 7.9 (1H, d);

LRMS 257, 259 (MH).

Preparation 4

(E)-3-(2-Amino-5-chloro-3-pyridinyl)-N-methyl-2-pronenamide

1-Hydroxybenzotriazole.$H_2O$ (196 mg, 1.4 mmol), methylamine.HCl (114 mg, 1.7 mmol), Hunig's base (1.58 ml, 9.1 mmol), 1-(3-dimethylaminopropyl)-3-ethylcarbodiimide.HCl (555 mg, 2.8 mmol) and (E)-3-(2-amino-5-chloro-3-pyridinyl)-2-propenoic acid.$CF_3CO_2H$ (438 mg, 1.4 mmol) were combined in DMF (5 ml) and stirred at RT for 16 h. The reaction mixture was poured into water (50 ml), extracted with EtOAc (3×20 ml), and the combined organic extracts washed with saturated brine, dried over $MgSO_4$, and concentrated to a yellow solid. Trituration with diethyl ether gave the title compound (198 mg, 0.9 mmol).

$^1$H ($\delta$, $d_6$-DMSO, 300 MHz) 2.7 (3H, d), 6.25 (2H, br s), 6.45 (1H, d), 7.4 (1H, d), 7.6 (1H, s), 7.87 (1H, br s), 7.9 (1H, s);

LRMS 212, 214 (MH);

M. Pt. 188–190° C.;

El. Anal.—Found: 50.88; H, 4.81; N, 19.75. Calcd for $C_9H_{10}ClN_3O$: C, 51.07; H, 4.76; N, 19.86.

The following compounds of Preparations 5–9 were prepared similarly:

Preparation 5

2-amino-N-benzylisonicotinamide

The title compound was prepared from 2-aminoisonicotinic acid (L. W. Deady, O. L. Korytsky, J. E. Rowe, *Aust. J. Chem.*, 1982, 35, 2025) and benzylamine:

$^1$H ($\delta$, $d_6$-DMSO, 300 MHz) 4.4 (2H, d), 6.05 (2H, s), 6.8 (1H, s), 6.8 (1H, d), 7.2–7.4 (5H, m), 8.0 (1H, d), 9.0 (1H, br t);

LRMS 228 (MH); 455 ($M_2H$).

Preparation 6

(E)-3-(2-Amino-5-chloro-3-pyridinyl)-N-benzyl-2propenamide

The title compound was prepared from (E)-3-(2-amino-5-chloro-3-pyridinyl)-2-propenoic acid and benzylamine as a yellow solid:

$^1$H ($\delta$, $d_6$-DMSO, 300 MHz) 4.2 (2H, d), 6.25 (2H, br s), 6.6 (1H, d), 7.2–7.35 (5H, m), 7.45 (1H, d), 7.65 (1H, s), 7.95 (1H, s), 8.4 (1H, br t);

LRMS 288, 290 (MH); 575, 577, 579 ($M_2H$);

El. Anal.—Found: C, 62.32; H, 4.93; N, 14.59. Calcd for $C_{15}H_{14}ClN_3O$: C, 62.61; H, 4.90; N, 14.60.

Preparation 7

(E)-3-(2-Amino-5-chloro-3-pyridinyl)-1-(3-hydroxypiperidino)-2-propen-1-one

The title compound was prepared from (E)-3-(2-amino-5-chloro-3-pyridinyl)-2-propenoic acid and 3-hydroxypiperidine as a white solid:

$^1$H (δ, d$_6$-DMSO, 400 MHz) 1.25–1.55 (2H, m), 1.6–1.95 (2H, m), 2.6–3.15 (1H, m), 3.2–4.3 (4H, m), 4.8–4.85 (1H, m), 6.3 (2H, s), 7.1–7.2 (1H, m), 7.5 (1H, d), 7.9 (1H, s), 8.0 (1H, d);

LRMS 282, 284 (MH); 563, 565, 567 (M$_2$H).

Preparation 8

(E)-3-(2-Amino-5-chloro-3-1pyridinyl)-N-benzyl-N-methyl-2-propenamide

The title compound was prepared from (E)-3-(2-amino-5-chloro-3-pyridinyl)-2-propenoic acid and N-methyl benzylamine as a yellow solid following crystallisation from diisopropyl ether:

$^1$H (δ, CDCl$_3$, 300 MHz) 3.1 (3H, s), 4.6–4.85 (4H, m), 6.8–6.85 (1H, m), 7.2–7.45 (6H, m), 7.5–7.7 (1H, m), 7.95–8.05 (1H, m);

LRMS 302, 304 (MH); 603 (M$_2$H);

M. Pt. 106–109° C.;

El. Anal.—Found: C, 63.33; H, 5.29; N, 13.67. Calcd for C$_{16}$H$_{16}$ClN$_3$O: C, 63.68: H, 5.34; N, 13.93.

Preparation 9

(E)-3-(2-Amino-5-chloro-3-pyridinyl)-1-morpholino-2-propen-1-one

The title compound was prepared from (E)-3-(2-amino-5-chloro-3-pyridinyl)-2-propenoic acid and morpholine as a yellow solid following crystallisation from isopropyl alcohol and trituration with diisopropyl ether:

$^1$H (δ, CDCl$_3$, 400 MHz) 3.6–3.8 (8H, m), 4.8 (2H, br s), 6.8 (1H, d), 7.55 (1H, s), 7.6 (1H, d), 8.0 (1H, s);

LRMS 268, 270 (MH).

Preparation 10

(E)-2-(2-Amino-5-chloro-3-pyridinyl)-N-methyl-1-ethenesulphonamide

A mixture of 3-bromo-5-chloro-2-pyridinamine (414 mg, 2 mmol), N-methyl ethene sulphonamide (266 mg, 2.2 mmol) and triethylamine (555 μl, 4 mmol), palladium acetate (18 mg, 0.08 mmol) and tri-o-tolylphosphine (50 mg, 0.16 mmol) in DMF (0.5 ml) in a Teflon™ pressure vessel was microwaved for 30 sec (full power), allowed to cool to RT and irradiated for a further 30 sec. After allowing to cool, the reaction mixture was diluted with water, extracted with EtOAc and the organic phase washed with saturated brine, dried over MgSO$_4$, and concentrated to a brown semi-solid. Purification by column chromatography on silica gel eluting with methylene chloride—methanol (95:5), and then crystallisation from methanol gave the title compound (130 mg, 0.5 mmol):

$^1$H (δ, d$_6$-DMSO, 400 MHz) 2.5 (3H, s), 6.5 (2H, br s), 6.95 (1H, br s), 7.1 (1H, d), 7.35 (1H, d), 7.95 (1H, s), 8.0 (1H, s);

LRMS 248, 250 (MH);

M. Pt. 194–8° C.;

El. Anal.—Found: C, 38.61; H, 4.04; N, 16.61. Calcd for C$_8$H$_{10}$ClNO$_2$S: C, 38.79; H, 4.07; N, 16.97.

The following compounds of Preparations 11–15 were prepared similarly:

Preparation 11

5-Chloro-3-[(E)-2-phenylethenyl]-2-pyridinamine

The title compound was prepared from 3-bromo-5-chloro-2-pyridinamine and stryene. Purification by column chromatography on silica gel eluting with hexane—EtOAc (70:30) gave an oil which crystallised from hexane to give 5-chloro-3-[(E)-2-phenylethenyl]-2-pyridinamine as a yellow solid:

$^1$H (δ, CDCl$_3$, 300 MHz) 4.5 (2H, br s), 6.9 (1H, d), 7.0 (1H, d), 7.2–7.55 (5H, m), 7.6 (1H, s), 8.0 (1H, s);

LRMS 231, 233 (MH);

El. Anal.—Found C, 67.33; H, 4.78; N, 12.00. Calcd for C$_{13}$H$_{11}$ClN$_2$: C, 67.68; H, 4.81; N, 12.14.

Preparation 12

5-Chloro-3-[(E)-2-(4-methoxyphenyl)ethenyl]-2-pyridinamine

The title compound was prepared from 3-bromo-5-chloro-2-pyridinamine and 4-methoxystryene. Purification by column chromatography on silica gel eluting with hexane—EtOAc (80:20) gave an oil which crystallised from hexane to give a yellow solid:

$^1$H (δ, CDCl$_3$, 300 MHz) 3.8 (3H, s), 4.5 (2H, br s), 6.75 (1H, d), 6.85–7.0 (3H, m), 7.4 (2H, d), 7.55 (1H, d), 7.95 (1H, d);

LRMS 261, 263 (MH).

Preparation 13

5-Chloro-3-[(E)-2-(2-pyridinyl)ethenyl]-2-pyridinamine

The title compound was prepared from 3-bromo-5-chloro-2-pyridinamine and 2-vinylpyridine. Purification by column chromatography on silica gel eluting with methylene chloride—methanol (95:5) and repeated using hexane—EtOAc (70:30 to 50:50) as eluant gave a yellow solid:

$^1$H (δ, CDCl$_3$, 300 MHz) 4.7 (2H, br s), 7.05 (1H, d), 7.2–7.35 (2H, m), 7.55 (1H, d) 7.5–7.7 (2H, m), 8.0 (1H, d), 8.6 (1H, d);

LRMS 232, 234 (MH).

Preparation 14

5-Chloro-3-[(E)-2-cyclohexylethenyl]-2-pyridinamine

The title compound was prepared from 3-bromo-5-chloro-2-pyridinamine and vinylcyclohexane. Purification by column chromatography on silica gel eluting with hexane—EtOAc (80:20) gave a pale yellow oil. An analytical sample was prepared by crystallisation from hexane:

$^1$H (δ, CDCl$_3$, 300 MHz) 1.1–1.4 (5H, m), 1.5–1.8 (5H, m), 2.1–2.2 (1H, m), 4.5 (2H, br s), 6.0–6.2 (2H, m), 7.4 (1H, d), 7.9 (1H, d);

LRMS 237, 239 (MH);

El. Anal.—Found: C, 65.85; H, 7.29; N, 11.84. Calcd for C$_{13}$H$_{17}$ClN$_2$: C, 65.95; H, 7.24; N, 11.83.

Preparation 15

3-[(E)-2-(2-Amino-5-chloro-3-pyridinyl)ethenyl]benzonitrile

The title compound was prepared from 3-bromo-5-chloro-2-pyridinamine and 3-cyanostryene. Methylene chloride extracts of the crude reaction mixture were concentrated and the desired product purified by column chromatography on silica gel eluting with methylene chloride—methanol (98:2) to give a yellow solid:

¹H (δ, CDCl₃, 300 MHz) 6.4 (2H, br s), 7.2 (1H, d), 7.35 (1H, d), 7.55 (1H, t), 7.7 (1H, d), 7.8–7.9 (3H, m), 8.15 (1H, s);

LRMS 256, 258 (MH);

M. Pt. >275° C.;

El. Anal.—Found: C, 65.49; H, 3.96; N, 16.21. Calcd for $C_{14}H_{10}ClN_3$: C, 65.76; H, 3.94; N, 16.43.

Preparation 16

3-[(E)-2-(1,3-Benzodioxol-5-yl)ethenyl]-5-chloro-2-pyridinamine

A solution of 3-bromo-5-chloro-2-pyridinamine (318 mg, 1.5 mmol), [(E)-2-(1,3-benzodioxol-5-yl)ethenyl](tributyl) stannane (250 mg, 1.7 mmol) (A. J. Bridges, A. Lee, C. E. Schwatrz, M. J. Towle, B. A. Littlefield, *Bioorg. Med. Chem.*, 1993, 1, 403), palladium acetate (19 mg, 0.08 mmol) and tri-o-tolylphosphine (50 mg, 0.16 mmol) in DMF (0.5 ml) and triethylamine (0.5 ml) in a teflon pressure vessel was heated in a microwave (full power) for 20 sec, allowed to cool to RT heated in a microwave for a further 20 sec and then 1 min 20 sec. After allowing to cool, the reaction mixture was poured into water (20 ml) and extracted with EtOAc (3×20 ml). The combined extracts were washed with water (2×20 ml), dried over MgSO₄ and concentrated. Recrystallisation from EtOAc—hexane gave the title compound as a brown solid (170 mg, 0.6 mmol):

¹H (δ, CDCl₃, 300 MHz) 4.55 (2H, br s), 6.0 (2H, s), 6.7 (1H, d), 6.8 (1H, d), 6.9–7.0 (2H, m), 7.05 (1H, s), 7.55 (1H, s), 7.95 (1H, s);

LRMS 275, 277 (MH).

Preparation 17

5-Chloro-3-(2-phenylethynyl)-2-pyridinamine

A solution of 3-bromo-5-chloro-2-pyridinamine (414 mg, 2.0 mmol), phenyl acetylene (225 mg, 2.2 mmol), copper (I) chloride (16 mg, 0.16 mmol), triethylamine (555 μl, 4.0 mmol) and dichlorobis(triphenylphosphine)palladium (II) (32 mg, 0.05 mmol) in DMF (0.5 ml) in a teflon pressure vessel was heated in a microwave (full power) for 30 sec, allowed to cool to RT and reheated for a further 30 sec. After cooling to RT, the reaction mixture was partioned between water—EtOAc. and the organic phase washed with sat. brine, dried over MgSO₄, and concentrated. Purification by column chromatography on silica gel eluting with methylene chloride—methanol (99:1) and subsequent crystallisation from hexane gave the title compound as a yellow solid (130 mg, 0.6 mmol):

¹H (δ, CDCl₃, 300 MHz) 5.0 (2H, br s), 7.3–7.4 (3H, m), 7.45–7.55(2H, m), 7.6 (1H, s), 8.0 (1H, br, s);

LRMS 229, 231 (MH);*

M. Pt. 119–119° C.;

El. Anal.—Found: C, 66.53; H, 3.91; N, 12.00. Calcd for $C_{13}H_9ClN_2+1/3$ water: C, 66.70; H, 4.13; N, 11.97.

Preparation 18

5-Chloro-3-phenoxy-2-pyridinamine

3-Bromo-5-chloro-2-pyridinamine (520 mg, 2.5 mmol), phenol (2.0 g, 21.3 mmol), potassium hydroxide (flakes, 85%, 600 mg, 9.1 mmol) and anhydrous copper (II) sulphate (100 mg, 0.6 mmol) and dimethoxyethane (250 μl) were heated together at 140° C. for 2 h, allowed to cool and the mixture poured into water (50 ml). EtOAc extracts (5×15 ml) were filtered through celite and extracted into 2N HCl (4×10 ml). The combined aqueous extracts were basified with NaOH and re-extracted into EtOAc (3×20 ml), dried over MgSO₄, and concentrated to a brown oil (230 mg). Purification by column chromatography on silica gel eluting with hexane—EtOAc (80:20) gave the title compound as a white solid (136 mg, 0.6 mmol). An analytical sample was prepared by crystallisation from hexane:

¹H (δ, CDCl₃, 400 MHz) 4.7 (2H, br s), 6.95 (1H, s), 7.05 (2H, d), 7.2 (1H, t), 7.4 (2H, dd), 7.8 (1H, s);

LRMS 221, 223 (MH);

El. Anal.—Found: C, 59.87; H, 4.11; N, 12.64. Calcd for $C_{11}H_9ClN_2O$: C, 59.87; H, 4.11; N, 12.70.

Preparation 19

3-(Benzyloxy)-5-chloro-2-pyridinamine (This compound is known and synthesis by a different route is disclosed—J. A. Bristol, I. Gross, R. G. Lovey, *Synthesis*, 1981, 971)

The title compound was prepared from 3-bromo-5-chloro-2-pyridinamine and benzyl alcohol using the conditions of preparation 18:

¹H (δ, CDCl₃, 300 MHz) 4.65 (2H, br s), 5.0 (2H, s), 6.95 (1H, s), 7.3–7.45 (5H, m), 7.6 (1H, s);

LRMS 235, 237 (MH):

El. Anal.—Found: C, 61.32; H, 4.70; N, 11.88. Calcd for $C_{12}H_{11}ClN_2O$: C, 61.41; H, 4.72; N, 11.94.

Preparation 20

2-[(2-Amino-5-chloro-3-pyridinyl)oxy]-1-ethanol

The title compound was by the method of G. Mattern (*Helv. Chimica Acta*, 1977, 60, 2062):

¹H (δ, CDCl₃, 300 MHz) 2.0 (1H, br s), 3.95–4.05 (2H, m), 4.14–4.2 (2H, m), 4.7 (2H, br s), 6.95 (1H, s), 7.7 (1H, br s);

LRMS 189, 191 (MH).

Preparation 21

5-Chloro-3-(2-methoxyethoxy)-2-pyridinamine

The title compound was by the method of G. Mattern (*Helv. Chimica Acta*, 1977, 60, 2062):

¹H (δ, CDCl₃, 300 MHz) 3.4 (3H, s), 3.7–3.8 (2H, m), 4.1–4.2 (2H, m), 4.7 (2H, br s), 6.95 (1H, s), 7.65 (1H, s);

LRMS 203, 205 (MH).

Preparation 22

2-[(2-Amino-5-chloro-3-2pyridinyl)oxy]-N-benzylacetamide

The title compound was prepared by the method of P. Nedenskov, N. Clauson-Kaas, J. Lei, H.-N. Heide, G. Olsen and G. Jansen (*Acta Chemica Scandinavica*, 1969, 23, 1791) from 2-amino-5-chloro-3-pyridinol (G. Mattern, *Helv. Chimica Acta*, 1977, 60, 2062) and N-benzyl-α-chloroacetamide. Sand coloured solid:

¹H (δ, CDCl₃, 400 MHz) 4.5–4.55 (2H, m), 4.6 (2H, s), 4.65 (2H, br s), 6.7 (1H, br s), 6.9 (1H, s), 7.2–7.35 (5H, m), 7.7 (1H, s);

LRMS 292, 294 (MH);

El. Anal.—Found: C, 56.92; H, 4.75; N, 13.93. Calcd for $C_{14}H_{14}ClN_3O_2+0.25$ water: C, 56.76; H, 4.93; N, 14.18.

Preparation 23

Methyl 3-[(2-amino-5-chloro-3-pyridinyl)oxy]methylbenzoate

The title compound was prepared using the method of Preparation 22 from 2-amino-5-chloro-3-pyridinol and methyl 3-(bromomethyl)benzoate to give a tan solid:

$^1$H ($\delta$, CDCl$_3$, 400 MHz) 3.9 (3H, s), 4.7 (2H, br s), 5.1 (2H, s), 6.95 (1H, s), 7.5 (1H, t), 7.6 (1H, d), 7.65 (1H, s), 8.05 (1H, d), 8.1 (1H, s);

LRMS 293, 295 (MH); 585, 587 (M$_2$H);

m. pt. 148–149.5° C.;

El. Anal.—Found: C, 57.08; H, 4.41; N, 9.42. Calcd for $C_{14}H_{13}ClN_2O_3$: C, 57.44, H, 4.48; N, 9.57.

Preparation 24

5-Chloro-3-(phenoxymnethyl)-2-pyridinamine

Sodium hydride (80% in oil, 124 mg, 4.1 mmol) was added portionwise to a solution of phenol (290 mg, 3.1 mmol) in anhydrous THF (15 ml). 5-Chloro-3-(chloromethyl)-2-pyridinamine.HCl (R. Herbert, D. G. Wibberley, *J Chem. Soc.*, 1969, 1504) (300 mg, 1.4 mmol) was then added and the reaction stirred at 50° C. for 3 h. After removal of THF in vacuo, the residue was partioned between diethyl ether and 1N NaOH. The aqueous phase was removed, extracted with diethyl ether and the combined organics washed with saturated brine, dried over MgSO$_4$ and concentrated to an oil which upon triturating with hexane gave the title compound as a white solid (265 mg, 1.1 mmol):

$^1$H ($\delta$, CDCl$_3$, 300 MHz) 4.85 (2H, br s), 4.9 (2H, s), 6.9–7.05 (3H, m), 7.25–8.05 (1H, s);

LRMS 235, 237 (MH);

Preparation 25

(2-Amino-3,5-dichloro-4-pyridinyl)methanol

To the hydrochloride salt of (2-amino-4-pyridinyl)methanol (J. M. Balkovec, M. J. Szymonifka, J. V. Heck, R. W. Ratcliffe; *J. Antibiotics*, 1991, 44, 1172) (3.2 g, 20 mmol) in conc HCl (22 ml) at 75–80° C. was added, over 30 mins, hydrogen peroxide (15% aq., 19.6 ml). After stirring at 80° C. for a further 3 h, the reaction mixture was cooled in an ice bath and the resultant yellow solid was removed by filtration, triturated with diisopropylether and diethyl ether to give the title compound as the hydrochloride salt (3.3 g, 14.3 mmol):

$^1$H ($\delta$, d$_6$-DMSO, 300 MHz) 4.55 (2H, s), 8.0 (1H, s);

LRMS 193, 195, 197 (MH);

M. Pt.218° C. dec.;

El. Anal.—Found: C, 31.36; H, 3.05; N, 11.97. Calcd for $C_6H_6Cl_2N_2O.HCl$: C, 31.40; H, 3.07; N, 12.21.

Preparation 26

3,5-Dichloro-4-(chloromethyl)-2-pyridinamine (2-Amino-3,5-dichloro-4-pyridinyl)methanol.HCl (2.2 g, 9.6 mmol) was stirred in thionyl chloride (5 ml) for 16 h at RT. The heterogeneous mixture was diluted with toluene. and the white solid removed by filtration, washed with diethyl ether and dried to give the title compound as the hydrochloride salt (2.27 g, 9.2 mmol):

$^1$H ($\delta$, d$_6$-DMSO, 300 MHz) 4.75 (2H, s), 8.05 (1H, s);

LRMS 211, 213, 215, 217 (MH);

m. pt. 208–210° C.;

El. Anal.—Found: C, 28.85; H, 2.48; N, 11.13. Calcd for $C_6H_5Cl_3N_2.HCl$: C, 29.06; H, 2.44; N, 11.30.

Preparation 27

3,5-Dichloro-4-(phenoxymethyl)-2-pyridinamine

Sodium phenoxide was prepared by the reaction of phenol (250 mg, 2.7 mmol) and sodium hydride (60% in oil, 106 mg, 2.7 mmol) in dry THF (15 ml) at RT. The solvent was removed in vacuo and replaced with dry DMF (10 ml), 3,5-dichloro-4-(chloromethyl)-2-pyridinamine (300 mg, 1.2 mmol) was added and the mixture heated to 60° C. for 2.5 h. After cooling to RT, the reaction mixture was diluted with water (15 ml) and extracted with diethyl ether (4×15 ml). The combined ethereal extracts were washed with water and saturated brine, dried over MgSO$_4$, then concentrated to a solid. This was crystallised from methylene chloride and hexane to give the title compound as a white solid (219 mg+2$^{nd}$ crop of 45 mg, 1.0 mmol):

$^1$H ($\delta$, CDCl$_3$, 300 MHz) 5.0 (2H, br s), 5.2 (2H, s), 6.95–7.05 (3H, m), 7.25–7.35 (2H, m), 8.05 (1H, s);

LRMS 269, 271, 273 (MH);

m. pt. 116–8° C.;

El. Anal.—Found: C, 53.10; H, 3.68; N, 10.33. Calcd for $C_{12}H_{10}Cl_2N_2O+0.1$ water: C, 53.20; H, 3.79; N, 10.34.

Preparation 28

N-[(2-Amino-3,5-dichloro-4-pyridinyl)methyl]-N-benzyl-N-methylamine 3,5-Dichloro-4-(chloromethyl)-2-pyridinamine.HCl (300 mg, 1.2 mmol) was stirred in N-benzylmethylamine (3 ml) at RT for 48 h after which the reaction mixture was diluted with water to give an oily precipitate. The supernatant liquor was removed, fresh water was added and again the aqueous layer removed. After trituration with hexane, the solid was dissolved in methylene chloride, dried over MgSO$_4$, and finally crystallised from methylene chloride—hexane to give the title compound as a fluffy white solid (190 mg, 0.6 mmol):

$^1$H ($\delta$, CDCl$_3$, 400 MHz) 2.15 (3H, s), 3.6 (2H, s). 3.75 (2H, s), 4.85 (2H, br s), 7.2–7.3 (5H, m), 7.9 (1H, s);

LRMS 296, 298, 300 (MH);

M. Pt. 124–6° C.;

El. Anal.—Found: C, 56.77; H, 5.10; N, 14.19. Calcd for $C_{14}H_{15}Cl_2N_3$: C, 56.44; H, 5.04; N, 14.06.

Preparation 29

3,5-Dichloro-4-(1-pyrrolidinylmethyl)-2-pyridinamine

The title compound was prepared using the method of preparation 28 using pyrrolidine. White solid:

$^1$H ($\delta$, CDCl$_3$, 400 MHz) 1.65–1.8 (4H, m), 2.6–2.7 (4H, m), 3.8 (2H, s), 4.9 (2H, br s), 7.95 (1H, s);

LRMS 246, 248, 250 (MH);

M. Pt. 98–101° C.;

El. Anal.—Found: C, 48.77; H, 5.32; N, 16.98. Calcd for $C_{10}H_{13}Cl_2N_3$: C, 48.79; H, 5.32; N, 17.07.

Preparation 30 t-butyl N-[(t-butoxycarbonyl)amino][(5-methyl-2-pyridinyl)imino]methylcarbamate To a solution of triethylamine (0.77 ml, 5.5 mmol) and 2-amino-5-picoline (200 mg, 1.8 mmol) in methylene chloride (20 ml) at 0° C. was added 1,3-bis(t-butoxycarbonyl)-2-methyl-2-thiopseudourea (0.59 g, 2.0 mmol) and mercury (II) chloride (0.55 g, 2.0 mmol). The reaction mixture was stirred at RT for 64 h, and the mercury residues filtered off for disposal. The filtrate was chromatographed on silica gel eluting with hexane—EtOAc (95:5 to 90:10) to give t-butyl N-[(t-butoxycarbonyl)amino][(5-methyl-2-pyridinyl)imino]methylcarbamate compound (111 mg, 0.32 mmol):

$^1$H ($\delta$, CDCl$_3$, 300 MHz) 1.5 (18H, s), 2.3 (3H, s), 7.5 (1H, br d), 8.1 (1H, d), 8.2 (1H, br s), 10.8 (1H,br s), 11.5 (1H,br s);

LRMS 351 (MH).

Other compounds of formula (IV; P and p$^1$ are both CO$_2$Bu$^t$) prepared by the same method are listed in Table 2 below.

All patents, patent applications, and publications cited above are incorporated herein by reference in their entirety.

TABLE 2

| Preparation | R² | R¹ | Mp °C. | Elemental Analysis | LRMS | ¹H, δ |
|---|---|---|---|---|---|---|
| 31 | H | Cl | — | — | 371(MH) | (CDCl₃, 300MHz) 1.5(18H, s), 7.65(1H, d), 8.25(1H, s), 8.5(1H, d), 10.9(1H, br s), 11.5(1H, br s) |
| 32 | H | Br | — | — | 415, 417(MH) | (CDCl₃, 300MHz) 1.5(9H, s), 1.5(9H, s), 7.8(1H, dd), 8.3(1H, d), 8.35(1H, d), 10.9(1H, br s), 11.45(1H, br s) |
| 33[a] | Ph | H | 158–160 | Found: C, 63.97; H, 6.82; N, 13.64. Calcd for C₂₃H₂₈N₄O₄; C, 64.05; H, 6.84; N, 13.58 | 413(MH) | (CDCl₃, 400MHz) 1.55(18H, s), 7.25–7.20(2H, m), 7.4–7.55(3H, m), 7.75–7.65(2H, m), 8.35(1H, d), 8.7(1H, br s) |
| 34 | CONHCH₂Ph | H | — | — | 470(MH) | (CDCl₃, 400MHz) 1.5(18H, s), 4.5(2H, d), 6.55(1H, br s), 7.25–7.35(5H, m), 7.5(1H, d), 8.4(1H, d), 8.7(1H, br s), 11.0(1H, br s), 11.45(1H, br s) |
| 35 | H | Cl | — | — | 405, 407, 409(MH) | (DMSO-d₆, 300MHz) 1.5(18H, s), 7.4(1H, s), 7.7(1H, s), 8.05(1H, br s), 11.8(1H, br s) |
| 36[b] | H | Br | — | — | 449, 451, 453(MH) | (CDCl₃, 300MHz) 1.5(18H, s), 7.9(1H, d), 8.2(1H, d), 8.4(1H, br s), 11.75(1H, br s) |
| 37[c] | H | Br | — | — | 449, 451, 453(MH) | (CDCl₃, 300MHz) 1.5(18H, s), 7.85(1H, d), 8.25(1H, br s) |
| 38 | E-CH=CH-CO₂Buᵗ | H | Cl | 180–181 | Found: C, 55.08; H, 6.63; N, 11.12. Calcd for C₂₃H₃₃ClN₄O₆ + 0.25 H₂O: C, 55.09; H, 6.773; N, 11.17 | 497(MH) | (CDCl₃, 300MHz) 1.5(18H, s), 1.55(9H, s), 6.6(1H, d), 7.8(1H, d), 8.2(1H, d), 8.25(1H, d), 10.1(1H, br s), 12.6(1H, br s) |
| 39 | CH₂CH₂CO₂Buᵗ | H | Cl | 106–8 | Found: C, 55.39; H, 7.09; N, 11.16. Calcd for C₂₃H₃₅ClN₄O₆: C, 55.36; H, 7.07; N, 11.23 | 499, 501(MH) | (CDCl₃, 300MHz) 1.4(9H, s), 1.5(18H, s), 2.65(2H, dd), 3.1(2H, dd), 7.5(1H, s), 8.1(1H, s) |
| 40 | E-CH=CHCONHMe | H | Cl | 175–7 | Found: C, 52.60; H, 6.15; N, 15.18. Calcd for C₂₀H₂₈ClN₅O₅: C, 52.92; H, 6.22; N, 15.43 | 454, 456(MH) | (CDCl₃, 300MHz) 1.55(18H, s), 2.95(3H, d), 6.4–6.5(1H, m), 7.5(1H, d), 7.7(1H, d), 8.1(1H, d), 8.25(1H, d), 10.1(1H, br s), 12.8(1H, br s) |
| 41 | E-CH=CHCONHCH₂Ph | H | Cl | — | Found: C, 58.57; H, 5.96; N, 13.11. Calcd for C₂₆H₃₂ClN₅O₅: C, 58.92; H, 6.09; N, 13.21 | 530, 532(MH) | (CDCl₃, 300MHz) 1.2–1.6(18H, br m), 4.55(2H, d), 6.6–6.75(1H, m), 7.2–7.35(5H, m), 7.5(1H, d), 7.7(1H, d), 8.15(1H, d), 8.45(1H, d), 10.2(1H, br s), 12.9(1H, br s) |
| 42 | E-CH=CHCO-(3-hydroxypiperidino) | H | Cl | 172–4 | Found: C, 54.09; H, 6.44; N, 13.05. Calcd for C₂₄H₃₄ClN₅O₆ + 0.5H₂O: C, 54.08; H, 6.62; N, 13.14 | 524, 526(MH) | (CDCl₃, 300MHz) 1.5(18H, s), 1.4–1.8(2H, m), 1.8–2.0(2H, m), 2.0–2.2(1H, br m), 3.4–4.0(5H, m), 7.6(1H, d), 7.75(1H, d), 8.1(1H, d) |
| 43 | E-CH=CHCON(Me)CH₂Ph | H | Cl | 166–7 | Found: C, 59.07; H, 6.32; N, 12.69. Calcd for C₂₇H₃₄ClN₅O₅ + 0.25H₂O): C, 59.11; H, 6.34; N, 12.76 | 554, 556(MH) | (CDCl₃, 400MHz) 1.5(18H, s), 2.95 & 3.2(3H, both s), 4.7 & 4.85(2H, both s), 7.2–7.3(5H, m), 7.7–7.9(2H, m), 8.15–8.2(2H, m), 10.1(1H, br s) |
| 44 | E-CH=CHCOmorpholino | H | Cl | — | — | 510, 512(MH) | (CDCl₃, 400MHz) 1.5(18H, s), 3.6–3.9(8H, m), 7.65(1H, d), 7.7(1H, s), 8.1(1H, d), 10.4(1H, br s), 12.9(1H, br s) |
| 45 | E-CH=CHSO₂NHMe | H | Cl | — | — | 490, 492(MH) | (CDCl₃, 400MHz) 1.55(18H, s), 2.85(3H, d), 4.3(1H, q), 7.45(1H, d), 7.65(1H, d), 8.2(1H, d), 8.55(1H, d), 10.15(1H, br s), 12.7(1H, br s) |
| 46 | E-CH=CHPh | H | Cl | 147–9 | Found: C, 60.87; H, 6.16; N, 11.85. Cacld for C₂₄H₂₉ClN₄O₄; C, 60.94; H, 6.18; N, 11.85 | 473(MH) | (CDCl₃, 300MHz) 1.6(18H, s), 7.2–7.4(4H, m), 7.7(2H, d), 7.9(1H, s), 8.05–8.1(2H, m), 10.05(1H, br s), 12.4(1H, br s) |
| 47 | E-CH=CH-(4-MeOC₆H₄) | H | Cl | — | Found: C, 59.12; H, 6.13; N, 10.97. Calcd for C₂₅H₃₁ClN₄O₅ + 0.25H₂O: C, 59.17; H, 6.26; N, 11.04 | 503, 505(MH) | (CDCl₃, 300MHz) 1.5(18H, s), 3.85(3H, s), 6.9(2H, d), 7.25(1H, d), 7.6(2H, d), 7.85(1H, d), 7.9(1H, d), 8.1(1H, d), 10.00(1H, br s), 12.4(1H, br s) |

TABLE 2-continued

| Preparation | R³ | R² | R¹ | Mp °C. | Elemental Analysis | LRMS | ¹H, δ |
|---|---|---|---|---|---|---|---|
| 48 | E-CH=CH-(2-pyridyl) | H | Cl | — | — | 474, 476(MH) | (CDCl₃, 300MHz) 1.5(18H, s), 7.1–7.2(1H, m), 7.6–7.8(2H, m), 7.8–8.0(2H, m), 8.15(1H, s), 8.25(1H, d), 8.5–8.55(1H, m), 10.1(1H, br s), 12.5(1H, br s) |
| 49 | E-CH=CH-chexyl | H | Cl | 114–116 | Found: C, 59.86; H, 7.30; N, 11.52. Calcd for C₂₅H₃₅ClN₂O₄: C, 60.17; H, 7.37; N, 11.70 | 479, 481(MH) | (CDCl₃, 300MHz) 1.1–1.9(28H, m), 2.1–2.3(1H, m), 6.2 & 6.35(1H, both dd), 7.15–7.3(2H, m), 7.7 & 7.75(1H, both s), 8.1 & 8.2(1H, both s), 10.0(1H, br s) |
| 50 | E-CH=CH-(3,4-methylenedioxyphenyl) | H | Cl | — | — | 517(MH) | (CDCl₃, 400MHz) 1.55(18H, s), 6.0(2H, s), 7.8(1H, d), 7.15(1H, s), 7.2–7.25(1H, m), 7.3(1H, s), 7.9(1H, s), 7.95(1H, d), 8.1(1H, s), 10.0(1H, br s), 12.4(1H, br s) |
| 51 | E-CH=CH(3-CN—C₆H₄) | H | Cl | 173–5 | Found: C, 59.95; H, 5.92; N, 13.62. Calcd for C₂₅H₂₈ClN₃O₄ + 0.1 DIPE⁽ᶠ⁾ 30 0.25H₂O: C, 59.97; H, 5.88; N, 13.66 | 498, 500(MH) | (CDCl₃, 400MHz) 1.55–1.6(18H, m), 7.35(1H, d), 7.45(1H, dd), 7.5(1H, d), 7.8(1H, d), 7.9(1H, d), 8.05(1H, s), 8.15(1H, d), 8.15(1H, d), 10.05(1H, br s), 12.4(1H, s) |
| 52 | C≡CPh | H | Cl | 144–6 | Found: C, 61.25; H, 5.80; N, 11.74. Calcd for C₂₄H₂₇ClN₂O₄: C, 61.20; H, 5.78; N, 11.90 | 471, 473(MH) | (CDCl₃, 300MHz) 1.5(18H, s), 7.3–7.4(3H, m), 7.7–7.9(3H, m), 8.1–8.3(1H, m), 12.0(1H, br s) |
| 53 | OPh | H | Cl | — | — | 463, 465(MH) | (CDCl₃, 400MHz) 1.5(18H, s), 7.1–7.3(4H, m), 7.35–7.45(2H, m), 8.05(1H, br s), 11–11.5(2H, br m) |
| 54 | OCH₂Ph | H | Cl | — | — | 477, 479(MH) | (CDCl₃, 400MHz) 1.5(18H, s), 5.15–5.25(2H, m), 7.15–7.25(1H, m), 7.3–7.4(2H, m), 7.5–7.6(2H, m), 7.85–8.0(1H, m), 10.1(1H, br s), 11.85(1H, br s) |
| 55 | OCH₂CH₂OH | H | Cl | 128–130 | Found: C, 49.97; H, 6.34; N, 12.71. Calcd for C₁₈H₂₇ClN₂O₆: C, 50.17; H, 6.32; N, 13.00 | 431, 433(MH) | (CDCl₃, 400MHz) 1.5(18H, s), 3.6–4.2(4H, br m), 7.15(1H, s), 7.2–7.3(1H, br s), 7.95(1H, s), 10.1(1H, br s) |
| 56 | OCH₂CH₂OMe | H | Cl | 164 | Found: C, 50.54; H, 6.54; N, 12.12. Calcd for C₁₉H₂₉ClN₂O₆ + 0.25H₂O: C, 50.77; H, 6.62; N, 12.47 | 445, 447(MH) | (CDCl₃, 400MHz) 4.15–4.25(2H, m), 7.15(1H, s), 7.9(1H, br s), 11.85(1H, br s) |
| 57 | OCH₂CONCH₂Ph | H | Cl | 178–180 | Found: C, 55.94; H, 5.99; N, 13.01. Calcd for C₂₅H₃₂ClN₃O₆: C, 56.23; H, 6.04; N, 13.12 | 534, 536(MH) | (CDCl₃, 300MHz) 1.4(9H, s), 1.55(9H, s), 4.6–4.7(4H, m), 7.1–7.3(6H, m), 7.95–8.0(1H, m), 8.75–8.85(1H, m), 10.1(1H, m), 12.4(1H, br s) |
| 58 | OCH₂(3-CO₂Me—C₆H₄) | H | Cl | 137.5–138 | Found: C, 56.06; H, 5.86; N, 10.33. Calcd for C₂₃H₃₁ClN₂O₇: C, 56.13; H, 5.84; N, 10.47 | 535, 537(MH) | (CDCl₃, 400MHz) 1.5(18H, s), 3.9(3H, s), 5.15–5.3(2H, br m), 7.2(1H, s), 7.5(1H, t), 7.8–8.1(4H, m), 11.7(1H, m) |
| 59 | CH₂OPh | H | Cl | 103–106 | Found: C, 58.16; H, 6.32; N, 11.42. Calcd for C₂₃H₂₉ClN₂O₅: C, 57.92; H, 6.13; N, 11.75 | 477, 479(MH) | (CDCl₃, 400MHz) 1.5(18H, s), 5.35(2H, s), 6.85–6.95(1H, m), 7.0(2H, d), 7.15–7.25(2H, m), 7.8(1H, s), 8.1(1H, s), 10.0(1H, br s), 11.9(1H, br s) |
| 60⁽ᵈ⁾ | Cl | Cl | Cl | — | Found: C, 44.41; H, 4.98; N, 12.18. Calcd for C₁₆H₂₁Cl₃N₂O₄ + ⅓EtAc: C, 44.32; H, 5.06; N, 12.02 | 439, 441, 443(MH) | (CDCl₃, 300MHz) 1.5(18H, s), 8.2(1H, s) |
| 61⁽ᵉ⁾ | Cl | Me | Cl | 106–8 | Found: C, 48.72; H, 5.77; N: 13.33. Calcd for C₁₇H₂₄Cl₂N₂O₄: C, 48.69; H, 5.77; N, 16.36 | 419, 421(MH) | (CDCl₃, 300MHz) 1.5(18H, s), 2.5(3H, s), 7.2(1H, s), 8.1(1H, br s), 8.3(1H, br s) |
| 62 | Cl | CH₂OPh | Cl | — | — | 511, 513, 515(MH) | (CDCl₃, 300MHz) 1.5(18H, s), 5.25(2H, s), 6.9–7.0(3H, m), 7.2–7.35(2H, m), 8.2–8.4(1H, m), 11.7(2H, br s) |
| 63 | Cl | CH₂NMeCH₂Ph | Cl | 136–7 | Found: C, 55.74; H, 6.10; N, 12.95. Calcd for C₂₃H₃₃Cl₂N₃O₄: C, 55.76; H, | 535, 540, 542(MH) | (CDCl₃, 300MHz) 1.5(18H, s), 3.15(3H, s), 3.6(2H, s), 3.8 & 3.9(2H, both s), 7.2–7.4(6H, m), 8.15 & 8.3(1H, br s) |

TABLE 2-continued

| Preparation | R³ | R² | R¹ | Mp ° C. | Elemental Analysis | LRMS | ¹H, δ |
|---|---|---|---|---|---|---|---|
| 64 | Cl | CH₂—N(CH₂)₄ | Cl | 142–4 | 6.18; N, 13.01 Found: C, 49.96; H, 6.30; N, 13.76. Calcd for $C_{21}H_{31}Cl_2N_5O_4$ + $1H_2O$: C, 49.80; H, 6.57; N, 13.83 | 488, 490, 492(MH) | (1H, both s), 11.75(1H, br s) (CDCl₃, 400MHz) 1.4–2.4(24H, br m), 2.4–3.0 (2H, br m), 3.6–4.7(2H, br m), 8.2–8.4(1H, br m), 10.2–13(2H, br m) |

[a]C. Li, L. S. Rittmann, A. S. Tsiftsoglou, K. K. Bhargava, A. C. Sartorelli, J. Med. Chem., 1978, 21, 874
[b]C. W Murtiashaw, R. Breitenbach, S. W. Goldstein, S. L. Pezzullo, G. J. Quallich, R. Sarges, J. Org. Chem., 1992, 57, 1930
[c]G. Mattern, Helv. Chim. Acta, 1977, 60, 2062
[d]K. S. Gudmundsson, J. M. Hinkley, M. S. Brieger, J. C. Drach, L. B. Townsend; Syn. Comm., 1997, 27, 861
[e]T. J. Kress, L. L. Moore, S. M. Costantino, J. Org. Chem., 1976, 41, 93.
[f]DIPE = diisopropylether.

What is claimed is:

1. A compound of formula (I):

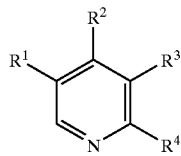

or a pharmaceutically acceptable salt thereof, or solvate of either entity,
wherein
- $R^1$ is H, halogen, CN, $C_{1-6}$ alkyl optionally substituted by one or more halogen, or $C_{1-6}$ alkoxy optionally substituted by one to three halogens,
- $R^2$ and $R^3$ are each independently H, halogen, $C_{1-6}$ alkyl optionally substituted by one or more halogen or $C_{1-6}$ alkoxy, $(C_n$-alkylene$)CO_2H$, $(C_n$-alkylene$)CO_2(C_{1-6}$ alkyl$)$, $(C_n$-alkylene$)CONR^5R^6$, $CH=CHR^7$, $CH=CHCO_2H$, $CH=CHCONR^5R^6$, $CH=CHSO_2NR^5R^6$, $C=CR^7$, $O(C_m$-alkylene$)OH$, $O(C_m$-alkylene$)OR^8$, $OR^8$, $O(C_m$-alkylene$)CONR^5R^6$, $CH_2OR^8$ or $CH_2NR^5R^6$,
- $R^4$ is $N=C(NH_2)_2$ or $NHC(=NH)NH_2$,
- $R^5$ and $R^6$ are each independently H, $C_{1-6}$ alkyl optionally substituted by OH or $CO_2H$
- $R^7$ is $C_{1-6}$ alkyl;
- $R^8$ is $C_{1-6}$ alkyl;
- n is 0, 1 or 2;
- m is 1 or 2;
- and wherein the "C-alkylene" linking groups in the definitions above are optionally substituted by one or more $C_{1-6}$ alkyl;

with the proviso that $R^1$, $R^2$ and $R^3$ are not all H.

2. A compound, salt or solvate according to claim 1 wherein $R^1$ is H, CN, halogen or methyl optionally substituted by one to three halogens.

3. A compound, salt or solvate according to claim 2 wherein $R^1$ is H, CN, Cl, Br or methyl.

4. A compound, salt or solvate according to claim 3 wherein $R^1$ is Cl or Br.

5. A compound, salt or solvate according to claim 1 wherein $R^2$ is H, halogen, $C_{1-6}$ alkyl optionally substituted by one to three halogens, $CH_2OR^8$, $(C_n$-alkylene$)CONR^5R^6$, $CO_2H$ or $CH_2NR^5R^6$.

6. A compound, salt or solvate according to claim 5 wherein $R^2$ is H, Cl, or methyl.

7. A compound, salt or solvate according to claim 6 wherein $R^2$ is H.

8. A compound, salt or solvate according to claim 1 wherein $R^3$ is H, Cl, Br, $CF_3$, $(C_n$-alkylene$)CO_2H$, $(C_n$-alkylene$)CO_2(C_{1-6}$ alkyl$)$, $(C_n$-alkylene$)CONR^5R^6$, $CH=CHR^7$, $CH=CHCO_2H$, $CH=CHCONR^5R^6$, $CH=CHSO_2NR^5R^6$, $C=CR^7$, $O(C_m$-alkylene$)OH$, $O(C_m$-alkylene$)OR^8$, $OR^8$, $O(C_m$-alkylene$)CONR^5R^6$, $CH_2OR^8$, or $CH_2NR^5R^6$.

9. A compound, salt or solvate according to claim 8 wherein $R^3$ is $CH=CHCO_2H$.

10. A compound, salt or solvate according to claim 1 wherein $R^1$ is H, CN, Cl, Br or methyl; $R^2$ is H, Cl, or methyl; and $R^3$ is $CH=CHCO_2H$.

11. A pharmaceutical composition comprising a compound, salt or solvate, as defined in any preceding claim, in admixture with a diluent or carrier.

12. A method of treating a condition mediated by uPA, which comprises administering an effective amount of a compound, salt or solvate as defined in claim 1 to a patient in need of said treatment, where the condition is infiltration of immune cells into inflammatory sites.

* * * * *

UNITED STATES PATENT AND TRADEMARK OFFICE
CERTIFICATE OF CORRECTION

PATENT NO.     : 6,583,162 B1
DATED          : June 24, 2003
INVENTOR(S)    : Dickinson et al.

It is certified that error appears in the above-identified patent and that said Letters Patent is hereby corrected as shown below:

Column 35,
Line 23, delete "C=CR$^7$" and insert instead -- C $\equiv$ CR$^7$ --.

Column 36,
Line 20, delete "C=CR$^7$" and insert instead -- C $\equiv$ CR$^7$ --.

Signed and Sealed this

Eighteenth Day of November, 2003

JAMES E. ROGAN
*Director of the United States Patent and Trademark Office*